US009249082B2

(12) United States Patent
Almusaiteer et al.

(10) Patent No.: US 9,249,082 B2
(45) Date of Patent: Feb. 2, 2016

(54) SYNTHESIS OF DIMETHYL CARBONATE FROM CARBON DIOXIDE AND METHANOL

(75) Inventors: Khalid A. Almusaiteer, Copley, OH (US); Sulaiman I. Al-Mayman, Riyadh (SA); Yousef S. Z. Alzeghayer, Riyadh (SA)

(73) Assignee: KING ABDULAZIZ CITY FOR SCIENCE AND TECHNOLOGY (KACST), Riyadh (SA)

( * ) Notice: Subject to any disclaimer, the term of this patent is extended or adjusted under 35 U.S.C. 154(b) by 556 days.

(21) Appl. No.: 12/966,017

(22) Filed: Dec. 13, 2010

(65) Prior Publication Data

US 2011/0196167 A1 Aug. 11, 2011

Related U.S. Application Data

(60) Provisional application No. 61/302,615, filed on Feb. 9, 2010.

(51) Int. Cl.
| | | |
|---|---|---|
| *C07C 69/96* | (2006.01) |
| *C07C 68/04* | (2006.01) |
| *B01J 23/28* | (2006.01) |
| *B01J 23/36* | (2006.01) |
| *B01J 23/42* | (2006.01) |
| *B01J 23/44* | (2006.01) |
| *B01J 23/46* | (2006.01) |
| *B01J 23/58* | (2006.01) |
| *B01J 23/63* | (2006.01) |
| *B01J 23/648* | (2006.01) |
| *B01J 23/755* | (2006.01) |
| *B01J 27/22* | (2006.01) |
| *B01J 29/44* | (2006.01) |
| *B01J 29/48* | (2006.01) |
| *B01J 35/00* | (2006.01) |
| *B01J 35/02* | (2006.01) |
| *B01J 35/10* | (2006.01) |
| *B01J 37/02* | (2006.01) |

(52) U.S. Cl.
CPC .............. *C07C 68/04* (2013.01); *B01J 23/28* (2013.01); *B01J 23/36* (2013.01); *B01J 23/42* (2013.01); *B01J 23/44* (2013.01); *B01J 23/464* (2013.01); *B01J 23/58* (2013.01); *B01J 23/63* (2013.01); *B01J 23/6482* (2013.01); *B01J 23/755* (2013.01); *B01J 27/22* (2013.01); *B01J 29/44* (2013.01); *B01J 29/48* (2013.01); *B01J 35/002* (2013.01); *B01J 35/006* (2013.01); *B01J 35/0013* (2013.01); *B01J 35/023* (2013.01); *B01J 35/1014* (2013.01); *B01J 35/1019* (2013.01); *B01J 35/1042* (2013.01); *B01J 35/1047* (2013.01); *B01J 37/0201* (2013.01)

(58) Field of Classification Search
None
See application file for complete search history.

(56) References Cited

U.S. PATENT DOCUMENTS

| | | |
|---|---|---|
| 3,114,762 A | 12/1963 | Mador et al. |
| 3,846,468 A | 11/1974 | Perrotti et al. |
| 4,582,645 A | 4/1986 | Spencer |
| 4,689,422 A | 8/1987 | Sawicki et al. |
| 4,900,705 A | 2/1990 | Sawicki et al. |
| 5,004,827 A | 4/1991 | Curnutt |
| 5,093,513 A | 3/1992 | Sawicki et al. |
| 5,149,856 A | 9/1992 | Schon et al. |
| 5,152,898 A | 10/1992 | Bartels |
| 5,171,874 A | 12/1992 | Smith et al. |
| 5,183,920 A | 2/1993 | Myers |
| 5,194,656 A | 3/1993 | Ancillotti et al. |
| 5,210,269 A | 5/1993 | Di Muzio et al. |
| 5,214,184 A | 5/1993 | Matuzaki et al. |
| 5,214,185 A | 5/1993 | Nishihira et al. |
| 5,218,135 A | 6/1993 | Buysch et al. |
| 5,227,510 A | 7/1993 | Watanabe et al. |
| 5,231,212 A | 7/1993 | Buysch et al. |
| 5,231,213 A | 7/1993 | Landscheidt et al. |
| 5,232,884 A | 8/1993 | Tanigawa |
| 5,233,072 A | 8/1993 | Kricsfalussy et al. |
| 5,235,087 A | 8/1993 | Klausener et al. |
| 5,274,163 A | 12/1993 | Rechner et al. |
| 5,283,351 A | 2/1994 | Kezuka et al. |
| 5,288,894 A | 2/1994 | Landscheidt et al. |
| 5,292,916 A | 3/1994 | Matsuzaki et al. |
| 5,292,917 A | 3/1994 | Nishihira et al. |
| 5,319,124 A | 6/1994 | Wolters et al. |
| 5,322,958 A | 6/1994 | Dreoni et al. |
| 5,338,878 A | 8/1994 | Pacheco et al. |
| 5,347,031 A | 9/1994 | Koyama et al. |
| 5,359,118 A | 10/1994 | Wagner et al. |
| 5,360,922 A | 11/1994 | Wolters et al. |

(Continued)

FOREIGN PATENT DOCUMENTS

| | | |
|---|---|---|
| BE | 1003167 | 12/1991 |
| CN | 1231216 | 10/1999 |

(Continued)

OTHER PUBLICATIONS

Fan et al., Applied Catalysis A: General, 372 (2010), pp. 94-102.*
Honda et al., Applied Catalysis A: General, 384 (2010), pp. 165-170.*
Aresta et al., Catalysis Today, 137 (2008), pp. 125-131.*
ScienceDirect, Applied Catalysis A: General homepage; URL: <http://www.sciencedirect.com/science/journal/0926860X> Accessed Nov. 18, 2013.*

(Continued)

Primary Examiner — Alicia L Otton
(74) Attorney, Agent, or Firm — Mark E. Bandy; Rankin, Hill & Clark LLP

(57) ABSTRACT

A method for producing dimethyl carbonate from methanol and carbon dioxide using a heterogeneous catalyst is described. The heterogeneous catalyst provides both acidic sites and basic sites. The reaction can be carried out at atmospheric pressure and relatively low temperatures.

11 Claims, 37 Drawing Sheets

(56) References Cited

U.S. PATENT DOCUMENTS

| | | | |
|---|---|---|---|
| 5,360,923 | A | 11/1994 | Nickel et al. |
| 5,380,906 | A | 1/1995 | Nishihira et al. |
| 5,387,708 | A | 2/1995 | Molzahn et al. |
| 5,391,803 | A | 2/1995 | King et al. |
| 5,395,949 | A | 3/1995 | Delledonne et al. |
| 5,403,949 | A | 4/1995 | Manada et al. |
| 5,405,986 | A | 4/1995 | Oda et al. |
| 5,414,104 | A | 5/1995 | Jentsch et al. |
| 5,426,209 | A | 6/1995 | Manada et al. |
| 5,430,170 | A | 7/1995 | Urano et al. |
| 5,436,362 | A | 7/1995 | Kondoh et al. |
| 5,449,806 | A | 9/1995 | Klausener et al. |
| 5,457,213 | A | 10/1995 | Delledonne et al. |
| 5,489,703 | A | 2/1996 | Pacheco et al. |
| 5,543,548 | A | 8/1996 | Landscheidt et al. |
| 5,550,278 | A | 8/1996 | Rechner et al. |
| 5,631,395 | A | 5/1997 | Rivetti et al. |
| 5,631,396 | A | 5/1997 | Nishihira et al. |
| 5,685,957 | A | 11/1997 | Rivetti et al. |
| 6,037,298 | A | 3/2000 | Hagen et al. |
| 6,452,036 | B1 | 9/2002 | Zaid et al. |
| 7,271,120 | B2 | 9/2007 | Sun et al. |
| 7,605,285 | B2 | 10/2009 | Kobayashi et al. |
| 7,674,742 | B2 | 3/2010 | Osora et al. |
| 2008/0249327 | A1 | 10/2008 | Eckelt et al. |

FOREIGN PATENT DOCUMENTS

| | | |
|---|---|---|
| CN | 1420112 | 5/2003 |
| CN | 1526693 | 9/2004 |
| CN | 1736596 | 2/2006 |
| EP | 0425197 | 5/1991 |
| EP | 0429675 | 6/1991 |
| EP | 0444293 | 9/1991 |
| EP | 0534545 | 3/1993 |
| EP | 0565076 | 10/1993 |
| EP | 0584785 | 3/1994 |
| EP | 0634386 | 1/1995 |
| EP | 0634387 | 1/1995 |
| EP | 0634390 | 1/1995 |
| EP | 0636601 | 2/1995 |
| EP | 0638541 | 2/1995 |
| EP | 0654462 | 5/1995 |
| EP | 0659731 | 6/1995 |
| EP | 1616855 | 1/2006 |
| EP | 1623758 | 2/2006 |
| EP | 1629888 | 3/2006 |
| JP | 2006438 | 1/1990 |
| JP | 2019347 | 1/1990 |
| JP | 2032045 | 2/1990 |
| JP | 2184655 | 7/1990 |
| JP | 2256651 | 10/1990 |
| JP | 3044353 | 2/1991 |
| JP | 3044354 | 2/1991 |
| JP | 3109358 | 5/1991 |
| JP | 4009356 | 1/1992 |
| JP | 4054156 | 2/1992 |
| JP | 4103561 | 4/1992 |
| JP | 4108765 | 4/1992 |
| JP | 4198141 | 7/1992 |
| JP | 4230243 | 8/1992 |
| JP | 4297443 | 10/1992 |
| JP | 4297445 | 10/1992 |
| JP | 4356446 | 12/1992 |
| JP | 5017410 | 1/1993 |
| JP | 5078284 | 3/1993 |
| JP | 5097773 | 4/1993 |
| JP | 5105642 | 4/1993 |
| JP | 5140047 | 6/1993 |
| JP | 5155819 | 6/1993 |
| JP | 5201930 | 8/1993 |
| JP | 5221929 | 8/1993 |
| JP | 5255201 | 10/1993 |
| JP | 5310644 | 11/1993 |
| JP | 5320098 | 12/1993 |
| JP | 5320099 | 12/1993 |
| JP | 6025080 | 2/1994 |
| JP | 6025104 | 2/1994 |
| JP | 6025105 | 2/1994 |
| JP | 6065146 | 3/1994 |
| JP | 6065155 | 3/1994 |
| JP | 6072966 | 3/1994 |
| JP | 6073582 | 3/1994 |
| JP | 6092906 | 4/1994 |
| JP | 6092907 | 4/1994 |
| JP | 6092908 | 4/1994 |
| JP | 6107601 | 4/1994 |
| JP | 6116209 | 4/1994 |
| JP | 6116212 | 4/1994 |
| JP | 6145103 | 5/1994 |
| JP | 6145113 | 5/1994 |
| JP | 6145114 | 5/1994 |
| JP | 6157408 | 6/1994 |
| JP | 6166661 | 6/1994 |
| JP | 6184055 | 7/1994 |
| JP | 6184056 | 7/1994 |
| JP | 6210181 | 8/1994 |
| JP | 6228026 | 8/1994 |
| JP | 6239806 | 8/1994 |
| JP | 6256265 | 9/1994 |
| JP | 6287166 | 10/1994 |
| JP | 6306018 | 11/1994 |
| JP | 6336460 | 12/1994 |
| JP | 6336461 | 12/1994 |
| JP | 6336462 | 12/1994 |
| JP | 6336463 | 12/1994 |
| JP | 6343870 | 12/1994 |
| JP | 6343871 | 12/1994 |
| JP | 6345696 | 12/1994 |
| JP | 7010811 | 1/1995 |
| JP | 7025830 | 1/1995 |
| JP | 7033715 | 2/1995 |
| JP | 7041457 | 2/1995 |
| JP | 7112134 | 5/1995 |
| JP | 7118210 | 5/1995 |
| JP | 7126220 | 5/1995 |
| JP | 7194983 | 8/1995 |
| JP | 7196581 | 8/1995 |
| JP | 8176071 | 7/1996 |

OTHER PUBLICATIONS

Khalid Almusaiteer, et al., "Isolation of Active Adsorbates for the No—Co Reaction on Pd/Al2O3 by Selective Enhancement and Selective Poisoning", Journal of Catalysis, 1998, pp. 161-170, vol. 180.

Steven A. Anderson, et al., "Kinetic studies of carbonylation of methanol to dimethyl carbonate over Cu+X zeolite catalyst", Journal of Catalysis, 2003, pp. 396-405, vol. 217.

Steven A. Anderson, et al., "The decomposition of dimethyl carbonate over copper zeolite catalysts", Applied Catalysis A: General, 2005, pp. 117-124, vol. 280.

Serena Bertarione, et al., "Surface reactivity of Pd nanoparticles supported on polycrystalline substrates as compared to thin film model catalysts: infrared study of CH3OH adsorption", Journal of Catalysts, 2004, pp. 64-73, vol. 223.

Daniel Bianchi, et al. "Intermediate species on zirconia supported methanol aerogel catalysts V. Adsorption of methanol", Applied Catalysis A: General, 1995, pp. 89-110, vol. 123.

Donald C. Bradley, "Metal Alkoxides as Precursors for Electronic and Ceramic Materials", Chemical Reviews, 1989, pp. 1317-1322, vol. 89, No. 6.

Attila J. Brungs, et al. "Dry reforming of methane to synthesis gas over supported molybdenum carbide catalysts", Catalysis Letters, 2000, pp. 117-122, vol. 70.

Jun-Chul Choi, et al. "Selective and high yield synthesis of dimethyl carbonate directly from carbon dioxide and methanol", The Royal Society of Chemistry, Green Chemistry, 2002, pp. 230-234, vol. 4.

Guan Hong Chu, et al. "Synthesis of dimethyl carbonate from carbon dioxide over polymer-supported iodide catalysts", Inorganica Chimica Acta, 2000, pp. 131-133, vol. 307.

(56) References Cited

OTHER PUBLICATIONS

Dean B. Clarke, et al., "Infrared Studies of the Mechanism of Methanol Decomposition on Cu/SiO2", Journal of Catalysis 1994, pp. 81-93, vol. 150.
P.A. Dilara, et al., "Structure sensitivity in the reaction of methanol on ZrO2", Surface Science, 1994, pp. 8-18, vol. 321.
Shunnong Fang, et al., "Direct synthesis of dimethyl carbonate from carbon dioxide and methanol catalyzed by base", Applied Catalysis A: General, 1996, pp. L1-L3, vol. 142.
Ian A. Fisher, et al., "A Mechanistic Study of Methanol Decomposition over Cu/SiO2, ZrO2/SiO2, and Cu/ZrO2/SiO2", Journal of Catalysis, 1999, pp. 357-376, vol. 184.
Ming-Yuan He, et al., "Temperature-Programmed Studies of the Adsorption of Synthesis Gas on Zirconium Dioxide", Journal of Catalysis, 1984, pp. 238-254, vol. 87.
Ming-Yuan He, et al., "Infrared Studies of the Adsorption of Synthesis Gas on Zirconium Dioxide", Journal of Catalysis, 1984, pp. 381-388, vol. 87.
Gamal A.M. Hussein, et al. "Infrared Spectroscopic Studies of the Reactions of Alcohols over Group IVB Metal Oxide Catalysts", J. Chem. Soc. Faraday Trans., 1991, pp. 2655-2659, vol. 87, No. 16.
Yoshiki Ikeda, et al., "Promoting effect of phosphoric acid on zirconia catalysts in selective synthesis of dimethyl carbonate from methanol and carbon dioxide", Catalysis Letters, 2000, pp. 59-62, vol. 66.
J. Juan-Juan, et al., "Catalytic activity and characterization of Ni/Al2O3 and NiK/Al2O3 catalysts for CO2 methane reforming", Applied Catalysis A: General, 2004, pp. 169-174, vol. 264.
Kyeong Taek Jung, et al., "An in Situ Infrared Study of Dimethyl Carbonate Synthesis from Carbon Dioxide and Methanol over Zirconia", Journal of Catalysis, 2001, pp. 339-347, vol. 204.
S. T. T King, "Reaction Mechanism of Oxidative Carbonylation of Methanol to Dimethyl Carbonate in Cu—Y Zeolite", Journal of Catalysis, 1996, pp. 530-538, vol. 161.
Jean Lamotte, et al., "Coadsorption of Methanol and Carbon Dioxide on Alumina", J. Chem. Soc., Faraday Trans., 1986, pp. 3019-3023, vol. 82.
Maela Manzoli, et al., "Decomposition and combined reforming of methanol to hydrogen: a FTIR and QMS study on Cu and Au catalysts supported on ZnO and TiO2", Applied Catalysis B: Environmental, 2004, pp. 201-209, vol. 57.
Graeme J. Millar, et al., "Infrared Study of the Adsorption of Methanol on Oxidised and Reduced Cu/SiO2 Catalysts", J. Chem. Soc. Faraday Trans., 1991, pp. 2795-2804, vol. 87, No. 17.
Yoshio Ono, "Dimethyl carbonate for environmentally benign reactions", Pure and Applied Chemistry, 1996, pp. 367-375, vol. 68, No. 2.
Yoshio Ono, "Catalysis in the production and reactions of dimethyl carbonate, an environmentally benign building block", Applied Catalysis A: General, 1997, pp. 133-166, vol. 155.
Michael A. Pacheco, et al., "Review of Dimethyl Carbonate (DMC) Manufacture and Its Characteristics as a Fuel Additive", American Chemical Society, Energy & Fuels, 1997, pp. 2-29, vol. 11.
J. Rasko, et al., "FTIR Study of the Interaction of Methanol with Clean and Potassium-Doped Pd/SiO2 Catalysts", Journal of Catalysis, 1994, pp. 22-33, vol. 146.
Ugo Romano, et al., "Synthesis of Dimethyl Carbonate from Methanol, Carbon Monoxide, and Oxygen Catalyzed by Copper Compounds", American Chemical Society, Ind. Eng. Chem. Prod. Res. Dev., 1980, pp. 396-403, vol. 19.
Jiang Ruixia, et al., "The effects of promoters on catalytic properties and deactivation-regeneration of the catalyst in the synthesis of dimethyl carbonate", Applied Catalysis A: General, 2003, pp. 131-139, vol. 238.

Yasushi Sato, et al., "Novel effective poly(2,2'-bipyridine-5,5'-diyl)-CuCl2 catalyst for synthesis of dimethyl carbonate (DMC) by oxidative carbonylation of methanol", Applied Catalysis A: General, 1999, pp. 219-226, vol. 185.
Yasushi Sato, et al., "A new type of support 'bipyridine containing aromatic polyamide' to CuCl2 for synthesis of dimethyl carbonate (DMC) by oxidative carbonylation of methanol", Journal of Molecular Catalysis A: Chemical, 2000, pp. 79-85, vol. 151.
Abbas-Alli G. Shaikh, et al., "Organic Carbonates", American Chemical Society, Chem. Rev., 1996, pp. 951-976, vol. 96.
Frigyes Solymosi, et al., "Analysis of the IR-Spectral Behavior of Adsorbed CO Formed in H2 + CO2 Surface Interaction over Supported Rhodium", 1987, pp. 312-322, vol. 104.
Frigyes Solymosi, et al., "FT-IR study on the interaction of CO2 with H2 and hydrocarbons over supported Re", Journal of Molecular Catalysis A: Chemical, 2005, pp. 260-266, vol. 235.
F. Solymosi, et al., "CO2 reforming of propane over supported Rh", Journal of Catalysis, 2003, pp. 377-385, vol. 216.
Keiichi Tomishige, et al., "CeO2—ZrO2 solid solution catalyst for selective synthesis of dimethyl carbonate from methanol and carbon dioxide", Catalysis Letters, 2001, pp. 71-74, vol. 76, No. 1-2.
Keiichi Tomishige, et al., "Catalytic Properties and Structure of Zirconia Catalysts for Direct Synthesis of Dimethyl Carbonate from Methanol and Carbon Dioxide", Journal of Catalysis, 2000, pp. 355-362, vol. 192.
Keiichi Tomishige, et al., "A novel method of direct synthesis of dimethyl carbonate from methanol and carbon dioxide catalyzed by zirconia", Catalysis Letters, 1999, pp. 225-229, vol. 58.
Keiichi Tomishige, et al., "Catalytic and direct synthesis of dimethyl carbonate starting from carbon dioxide using CeO2—ZrO2 solid solution heterogeneous catalyst: effect of H2O removal from the reaction system", Applied Catalysis A: General, 2002, pp. 103-109, vol. 237.
Pietro Tundo, et al., "Gas-Liquid Phase-Transfer Catalysis: A New Continuous-Flow Method in Organic Synthesis", American Chemical Society, Ind. Eng. Chem. Res., 1989, pp. 881-890, vol. 28.
H.Y. Wang, et al., "Carbon dioxide reforming of methane to syngas over SiO2-supported rhodium catalysts", Applied Catalysis A: General, 1997, pp. 239-252, vol. 155.
Mouhua Wang, et al., "Synthesis of dimethyl carbonate from urea and methanol over solid base catalysts", Catalysis Communications, 2006, pp. 6-10, vol. 7.
X.L. Wu, et al., "Direct synthesis of dimethyl carbonate (DMC) using Cu-Ni/VSO as catalyst", Journal of Molecular Catalysis A: Chemical, 2006, pp. 93-97, vol. 249.
Noboru Yamazaki, et al., "Polymers Derived from Carbon Dioxide and Carbonates", American Chemical Society, Ind. Eng. Chem. Prod. Res. Dev., 1979, pp. 249-252, vol. 18, No. 4.
Lin-Chiuan Yan, et al., "Synthesis and characterization of aerogel-derived cation-substituted barium hexaaluminates", Applied Catalysis A: General, 1998, pp. 219-228, vol. 171.
Rong Zhang, et al., "In situ FTIR studies of methanol adsorption and dehydrogenation over Cu/SiO2 catalyst", Fuel, 2002, pp. 1619-1624, vol. 81.
Tiansheng Zhao, et al., "Novel reaction for dimethyl carbonate synthesis from CO2 and methanol", Fuel Processing Tehnology, 2000, pp. 187-194, vol. 62.
Weiging Zou, et al., "The effect of precursor structure on the preparation of Pt/SiO2 catalysts by the sol-gel method", Materials Letters, 1995; pp. 35-39, vol. 24.
Khalid Almusaiteer; Synthesis of dimethyl carbonate (DMC) from methanol and CO2 over Rh-supported catalysts; Catalysis Communications, 10 (2009) 1127-1131; Riyadh College of Technology; Riyadh, SA.

* cited by examiner

SYNTHESIS OF DIMETHYL CARBONATE FROM CARBON DIOXIDE AND METHANOL

CROSS REFERENCES TO RELATED APPLICATIONS

This application claims priority upon U.S. provisional application Ser. No. 61/302,675 filed Feb. 9, 2010.

FIELD OF THE INVENTION

The present invention relates to methods of producing dimethyl carbonate from carbon dioxide and methanol. The methods utilize a particular class of heterogeneous catalysts.

BACKGROUND OF THE INVENTION

Catalysts play a key role in increasing the efficiency of chemical synthesis and processing by lowering the reaction temperature and pressure, increasing product yield, and reducing by-product formation. Development of environmentally benign synthesis processes that eliminate toxic feed stocks, combine process steps, and result in a net reduction of pollutants and energy use rests on, to a great extent, the ability for innovation in the design of synthesis pathways and their catalyst.

$CO_2$ utilization is an important process from the viewpoint of green chemistry. The objective of $CO_2$ utilization is to design an efficient chemical process for conversion of captured $CO_2$ to useful products. $CO_2$ can participate in many chemical reactions that lead to useful products. Among these reaction processes is the dimethyl carbonate (DMC) synthesis.

DMC is an important raw material with versatile applications as a nontoxic substitute for toxic and corrosive agents such as dimethyl sulfate, dimethyl halides, and phosgene in methylation and carbonylation processes. In addition, phasing out methyl tert-butyl ether (MTBE) has led to consideration of DMC as an environmentally friendly, oxygenated fuel additive, i.e. octane enhancer, due to its high octane number, low toxicity, and quick biodegradabillity. DMC has an oxygen content three times that of MTBE (53 wt % vs. 18 wt %) so that on a weight basis only one third as much DMC is required to achieve the same oxygen level as MTBE.

DMC is a very good blending component, which has very high oxygen content (53 wt %) for environmental gasoline. Recently, automotive emission testing with DMC indicated that DMC is a more effective oxygenate than MTBE. DMC reduced total hydrocarbon and CO emission more than MTBE at the same weight percent of oxygen in the fuel. Therefore approximately 4.5 times less volume of DMC is required as compared to MTBE at the same weight percent oxygen in the fuel. Formaldehyde emission was also lower with DMC than with MTBE. DMC also exhibits good blending with octane.

DMC is classified as slightly toxic and is a more effective oxygenate than MTBE at the same weight percent oxygen in the fuel. In addition, DMC has a low emission of CO and $NO_x$ in automobile exhaust. The solubility of DMC in water is slight, whereas the solubility of MTBE is 4.3 wt %, which leads to MTBE accumulating in ground water.

Developing an environmentally friendly process and an effective catalyst is key for creating an economical and efficient technology for converting $CO_2$ to DMC.

The DMC amount needed by a typical major refiner company to increase the oxygen content of its gasoline by 1 wt % is approximately 10,000 bbl/day. However, the total worldwide production capacity of DMC is estimated at about 1000 bbl/day.

Currently, DMC is primarily produced by oxidative carbonylation of methanol over CuCl. The main problems with this process are the low per-pass conversion, corrosion by chloride, and the presence of chloride in the DMC product. Another route for DMC production is oxidative carbonylation using nitric oxide. The major concern with this process is the use of nitric oxide. DMC can also be synthesized by (i) the reaction of methanol with phosgene, (ii) oxidative carbonylation of methanol by CO and $O_2$ with the use of Cu and/or Pd catalysts, and (iii) co-production of DMC and ethylene glycol through the transesterification of ethylene carbonate with methanol. These routes use poisonous, flammable, and corrosive material such as phosgene, hydrogen chloride, carbon monoxide, and nitric oxide. Also, they carry potential explosion hazards.

An oxidative carbonylation process for producing DMC from $CO_2$ and methanol has been developed. In this reaction route, a copper chloride catalyst system is used. The reaction is basically a redox system in which copper catalyst, as cuprous chloride, is oxidized by elemental oxygen, in the presence of methanol, to cupric methoxychloride, which is then reduced with carbon monoxide to form dimethyl carbonate and to restore the cuprous chloride. Both reactions take place simultaneously. The reactions of the process can be summarized as follows:

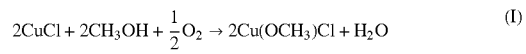

$$2CuCl + 2CH_3OH + \frac{1}{2}O_2 \rightarrow 2Cu(OCH_3)Cl + H_2O \qquad (I)$$

$$2Cu(OCH_3)Cl + CO \rightarrow CH_3OCOOCH_3 + 2CuCl \qquad (II)$$

The overall reaction is:

$$2CH_3OH + CO + \frac{1}{2}O_2 \rightarrow CH_3OCOOCH_3 + H_2O \qquad (III)$$

The process is believed to take place in a series of liquid-filled continuous stirred tank reactors, operating at approximately 393 K (120° C.) and a pressure of 27 atmospheres (2735 $KN/m^2$). Since the oxygen is the limiting reagent, it must be fed at a carefully controlled rate. The maximum content of oxygen must not exceed 4 mol % at any point in the system to avoid the potential for explosion.

The main problems with this process are the low per-pass conversion, corrosion by chloride, and the presence of chloride in the DMC product.

A similar oxidative carbonylation route to the previous strategy has been developed. In this technology, nitric oxide (NO) is used as a redox coupling agent for the formation of dimethyl oxalate (DMO) and dimethyl carbonate (DMC). This technology has been developed and commercialized mainly to produce DMO. The DMO catalyst system was modified later to give high selectivity to DMC. A 4500 metric ton/year plant for DMC synthesis has been built. The reaction conditions of the process are in the range of 1-20 atmospheres and 323-423 K (50 to 150° C.), where the catalysts used were equimolar amounts of palladium chloride and a second metal chloride (Fe or Cu). These catalysts were co-impregnated on an active carbon support. The reactions of the process are thought to proceed as follows:

In a first step, methanol is reacted with oxygen and NO to form methyl nitrite (MN) and water:

$$2CH_3OH + 2NO + \frac{1}{2}O_2 \rightarrow 2CH_3ONO + H_2O \quad (IV)$$

In a second step, gaseous methyl nitrite reacts with a mole of carbon monoxide over the bimetallic catalyst to form DMC and restore the original NO:

$$2CH_3ONO + CO \rightarrow CH_3OCOOCH_3 + 2NO \quad (V)$$

The overall reaction is:

$$2CH_3OH + CO + \frac{1}{2}O_2 \rightarrow CH_3OCOOCH_3 + H_2O \quad (VI)$$

This latter technology has particular advantages over the first noted strategy. A major advantage of the latter system lies in a dual reactor scheme, where the feed methanol and the water by-product never pass over the metal chloride catalyst. On the other hand, in the former system, water deactivation of the catalyst limits conversion to 15-20%. By separating the water from feed gas, the per pass conversion of the methyl nitrite can approach 100% without significant catalyst deactivation. Also, the latter process takes particular advantage of the fact that the redox reagent is a gas in both of its states as NO and $CH_3ONO$. The similar species in the former process are solids, i.e. CuCl and $Cu(OCH_3)Cl$. The simplicity of vapor/liquid separation compared to solid/liquid separation benefits the latter process. However, extreme care must be considered when mixing the three reactants (methanol, nitric oxide and oxygen) to stay outside the explosion limits of the reaction. Methyl nitrite is also highly reactive and must be handled with care. The use of the latter route also results in additional toxicity concerns due to the use of nitric oxide.

It is also known to form dimethyl carbonate (DMC) by a transesterification reaction between ethylene carbonate and methanol, with ethylene glycol as a co-product:

$$C_2H_4CO_3 + 2CH_3OH \rightarrow CH_3OCOOCH_3 + C_2H_4(OH)_2 \quad (VII)$$

It also is possible to produce DMC by the methanolysis of urea. The tin-catalyzed reaction of methanol with urea to give DMC is a well known synthesis. The reactions of the process can be illustrated as follows:

$$(NH_2)_2CO + CH_3OH \rightarrow H_2NCOOCH_3 + NH_3 \quad (VIII)$$

$$H_2NCOOCH_3 + CH_3OH \rightarrow CH_3OCOOCH_3 + NH_3 \quad (IX)$$

The overall reaction can be presented as follows:

$$(NH_2)_2CO + 2CH_3OH \rightarrow CH_3OCOOCH_3 + 2NH_3 \quad (X)$$

However, this reaction is not thermodynamically favorable as the ideal gas free energy change ($\Delta G$) for this reaction is +3.2 kcal/mol at 373K (100° C.). The first methanolysis step (reaction VIII) to methyl carbamate is favored, but dimethyl carbonate (reaction IX) is not favored. Moreover, the chemistry is thermodynamically unfavorable and an additional driving force will be required in order to achieve reasonable conversion levels.

Two other technologies also have attractive possibilities for DMC production. These are: (i) the use of supported copper on carbon catalyst, which occurs in the gas phase and avoids the need for solid-liquid separation, but the catalyst deactivation is a major problem; and (ii) the alkylene carbonate routes which are attractive because they start with two relatively low cost materials, i.e. ethylene and carbon dioxide.

The direct synthesis of DMC starting from alcohols and carbon dioxide was studied since the 1980s. This route for DMC synthesis from inexpensive feedstocks such as $CO_2$ and methanol (as shown below) is challenging:

$$2CH_3OH + CO_2 \rightarrow (CH_3O)_2CO + H_2O \quad (XI)$$

It has been reported that DMC can be produced from $CO_2$ and methanol in the presence of various catalysts, such as dialkylin dialkoxides, tin(IV), tetra-alkoxides, titanium(IV) tetra-alkoxides, bases, a mixture of palladium(II) chloride and copper(II) acetate, and thallium(I) hydroxide and alkali metal iodides. However, these reaction systems are homogeneous, which present three major problems: (a) difficulty in catalyst recovery, (b) reaction conditions of high pressure, and (c) rapid deactivation of the catalyst by process excursions.

Recently, catalytic DMC synthesis starting from carbon dioxide and methanol has been studied over zirconia ($ZrO_2$) catalysts. The effectiveness of this catalyst was attributed to the presence of both acidic and basic sites. It was proposed that basic sites are required to activate methanol and $CO_2$, and that acidic sites are required to supply methyl groups from methanol in the last step of the reaction mechanism. However, the selectivity and yield of this reaction was far from satisfactory.

Accordingly, a need exists for an improved process for producing dimethyl carbonate. Specifically, it would be desirable to provide an economical process for producing dimethyl carbonate from carbon dioxide and methanol, without the numerous problems associated with currently known strategies.

SUMMARY OF THE INVENTION

The difficulties and drawbacks associated with previously known reaction techniques and catalysts addressed in the present methods and catalysts.

In one aspect, the invention provides a method for producing dimethyl carbonate. The method comprises providing effective amounts of methanol and carbon dioxide to a reaction vessel. The method also provides reacting methanol and carbon dioxide in the presence of a heterogeneous catalyst in the reaction vessel to produce dimethyl carbonate.

In another aspect, the invention provides a method for producing dimethyl carbonate using a heterogeneous catalyst. The method comprises providing an effective amount of methanol to a reaction vessel. The method also comprises providing an effective amount of carbon dioxide to the reaction vessel. And, the method comprises reacting the methanol and the carbon dioxide in the presence of a heterogeneous catalyst to thereby produce dimethyl carbonate. The heterogeneous catalyst provides acidic reaction sites and basic reaction sites.

As will be realized, the invention is capable of other and different embodiments and its several details are capable of modifications in various respects, all without departing from the invention. Accordingly, the drawings and description are to be regarded as illustrative and not restrictive.

DETAILED DESCRIPTION OF THE EMBODIMENTS

Figure 1A:
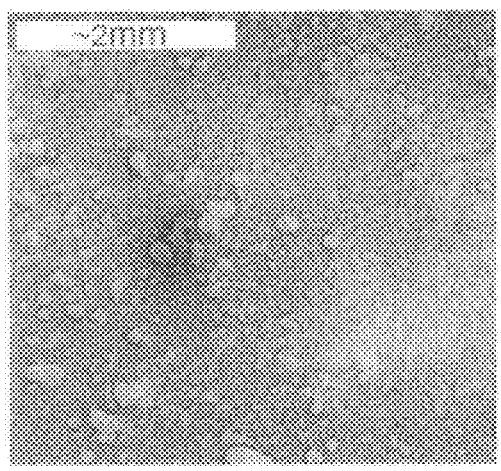
FIGS. 1A-1D are SEM images of a catalyst system 5% $Rh/Al_2O_3$.
Figure 1B:
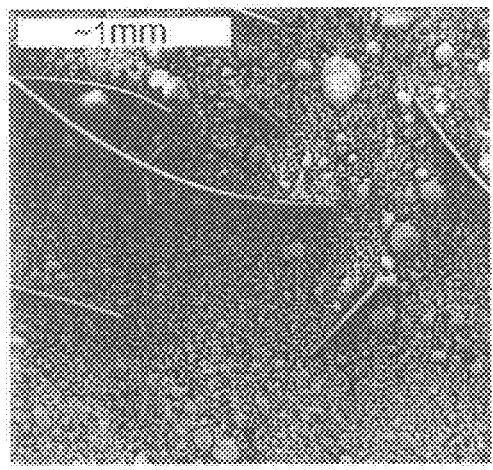
Figure 1C:
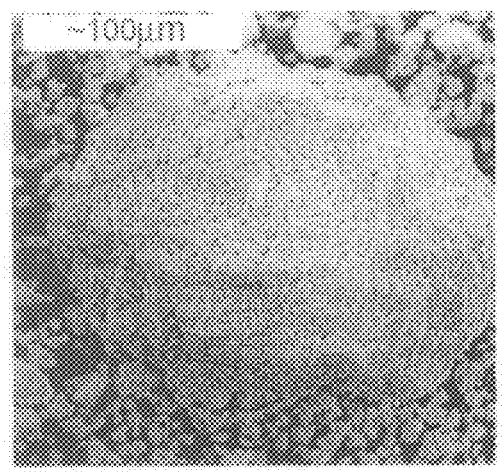
Figure 1D:
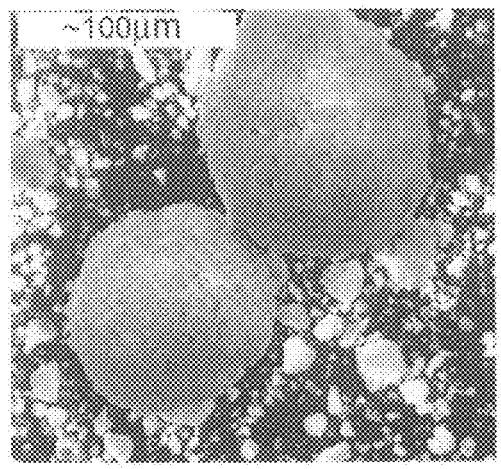

Certain heterogeneous catalyst systems that provide both acidic sites and basic sites for various reaction species have been discovered which enable the production of dimethyl carbonate from methanol and carbon dioxide. The catalyst systems are typically supported, however the invention includes certain unsupported catalyst systems. The methods for forming dimethyl carbonate can be performed at relatively low temperatures. Although the present invention and its various and assorted preferred aspects are primarily described herein in terms of producing dimethyl carbonate, it will be appreciated that the invention may also encompass the production of other alkyl carbonates and thus, is not specifically limited to dimethyl carbonate.

It has also been surprisingly discovered that the removal of water produced as a by-product in the synthesis of dimethyl carbonate is a key to accomplishing a high conversion by shifting the equilibrium to dimethyl carbonate. Dehydration is successfully carried out by circulating the reaction mixture through a dehydrating tube packed with molecular sieve 3 Å. Under effective dehydrations, the DMC yield is almost linearly dependent on: reaction time, catalyst amount, methanol concentration, and $CO_2$ pressure.

Methanol adsorption and dissociation also play an important role in the DMC synthesis from methanol and $CO_2$. Adsorption and decomposition of methanol is likely influenced by the surface structure of the catalyst, i.e., structure-sensitive reaction. Numerous studies have suggested that the primary step in methanol dissociation is rupture of the O—H and C—O bonds. As a result, formation of methoxy species ($CH_3O$) and other products has been reported. The methoxy species decomposes to carbon monoxide and hydrogen at higher temperatures. Although not wishing to be limited to any particular theory, it is believed that the presence of oxygen on the catalyst surface seems to promote $CH_3OH$ dissociation and formation of a methoxy species, which undergoes decomposition instead of associative desorption as $CH_3OH$.

Investigations of methanol adsorption and decomposition have been performed on $Cu/SiO_2$, $ZrO_2$, and $CuO/ZrO_2$. It has also been reported that methanol adsorption on $Cu/SiO_2$ at 295K (22° C.) resulted in the formation of methoxy species on both Cu and $SiO_2$. Heating the adsorbed species to 393 K (120° C.) led to the loss of methoxy species on Cu and the appearance of formate species on Cu. Further heating to 538 K (265° C.) produced gas-phase and adsorbed methyl formate, as well as $CO_2$ and CO. It has also been shown that methanol decomposition on $Cu/SiO_2$ produces adsorbed methoxy, formaldehyde, methylenebisoxy, and formate groups on Cu upon methanol adsorption at 303 K (30° C.). For zirconia, it was reported the appearance of methoxy species upon exposure to methanol at 298 K (25° C.). During temperature-programmed desorption of adsorbed methanol, CO, $CH_4$, $CH_3OH$, and $CH_2O$ peaks were observed at 453 K (180° C.). CO, $CO_2$, $CH_4$, $H_2$, and $H_2O$ were observed at 773 K (500° C.), and additional CO and $CO_2$ formation was observed at 863 K (590° C.). Methoxy decomposition was found to occur at 523-573 K (250 to 300° C.), with the formation of CO and $CO_2$ at higher temperatures.

A bifunctional catalysis on $CuO/ZrO_2$ has been observed during methanol adsorption and decomposition, where zirconia provides adsorption sites for reaction intermediates and Cu is proposed to facilitate the transfer and utilization of hydrogen. Methanol adsorption on $CuO/ZrO_2$ and $ZrO_2$ was shown to result in the formation of methoxy species on zirconia at 298 K (25° C.), which are converted to formate and carbonate species on zirconia and finally to gas-phase CO, $CO_2$, $H_2$, and $H_2O$ at higher temperatures. It was observed that the transformation of methoxy species to formate and carbonate species occurs at lower temperatures when Cu is present. The spillover of hydrogen from Cu was envisioned to restore OH groups on zirconia, which react with methoxy, resulting in formate and carbonate formation. In the absence of Cu, OH groups on zirconia are depleted, resulting in less efficient methoxy conversion.

In accordance with the present invention, various catalyst systems have been discovered for use in synthesizing dimethyl carbonate. Preferably, these catalyst systems are heterogeneous and provide both acidic sites and basic sites. The catalyst is preferably Rh, Rh—K, Ni, $Mo_2C$, Pd, Pt, Re, $MoO_3$, and combinations thereof. More specifically, these catalyst systems include, but are not limited to Rh-supported catalysts, Ni-supported catalysts, Pd-supported catalysts, Pt-supported catalysts, Re-supported catalysts, $Mo_2C$-supported and unsupported catalysts, and $MoO_3$-supported and unsupported catalysts.

A wide variety of supports can be used in the preferred catalysts. For example, the support can be one or more of $SiO_2$, $Al_2O_3$, ZSM-5, $V_2O_5$, $TiO_2$, $ZrO_2$, and combinations thereof. In certain embodiments of the invention, the support is formed by a sol-gel method.

More specifically, it has been discovered that $Rh/Al_2O_3$, and $Ni/SiO_2$—$Al_2O_3$ are active towards the DMC synthesis. In addition to $Rh/Al_2O_3$, and $Ni/SiO_2$—$Al_2O_3$, the $Mo_2C/Al_2O_3$ catalyst (proved to be successful in a coupling reaction) has been evaluated and was found to be active towards the DMC synthesis from methanol and $CO_2$. Additional preferred catalyst systems in accordance with the invention include, but are not limited to $Rh/Al_2O_3$ (sol gel), $Pd/Al_2O_3$ (sol gel), $Pt/Al_2O_3$ (sol gel), $Ni/Al_2O_3$ (sol gel), $Rh/SiO_2$, Rh/ZSM-5 and Rh—$K/Al_2O_3$. Moreover, additional preferred catalyst systems include, but are not limited to $Pd/V_2O_5$, $Pd/TiO_2$, $Pd/TiO_2$—$V_2O_5$, $Pd/TiO_2$—$ZrO_2$, $Pt/Al_2O_3$, $Re/Al_2O_3$, $MoO_3/Al_2O_3$, $MoO_3/ZSM-5$, and $MoO_3/SiO_2$.

The surface morphology and physical properties were examined for different catalyst samples that showed activity towards DMC synthesis from methanol and $CO_2$. The surface area and pore size data are summarized in Table 1. A weak C peak was observed in almost all spectra and was not considered for compositional calculations. The SEM and EDX results are also summarized herein. Details as to various procedures and analytical techniques are set forth herein in the Examples section.

5% $Rh/Al_2O_3$

Figure 2A:
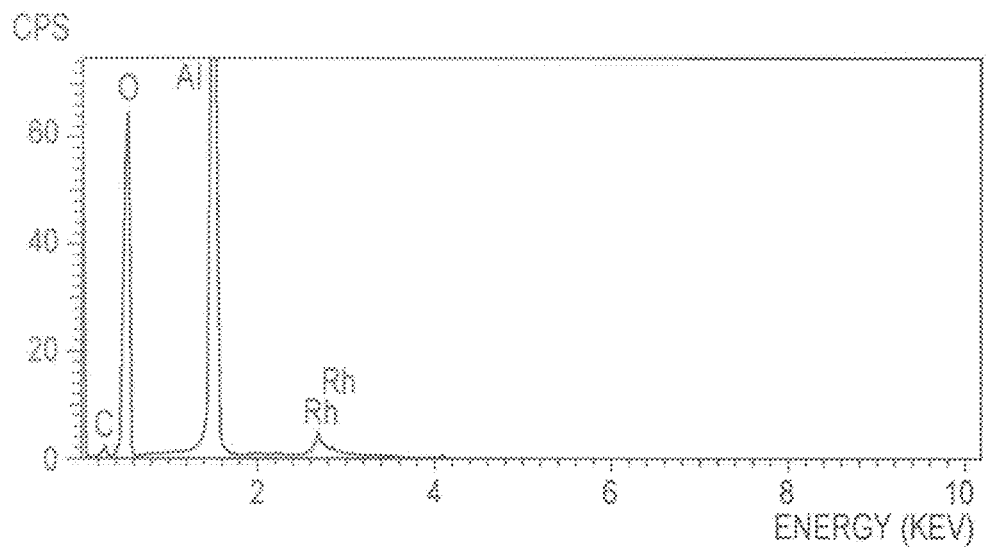
FIGS. 2A-2B are EDX spectra for 5% $Rh/Al_2O_3$.
Figure 2B:
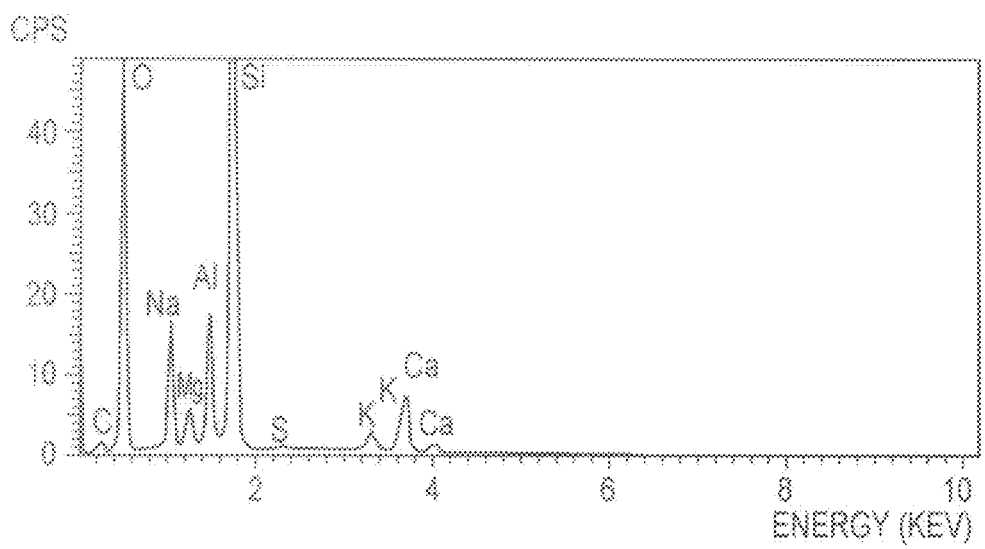
Figure 3A:
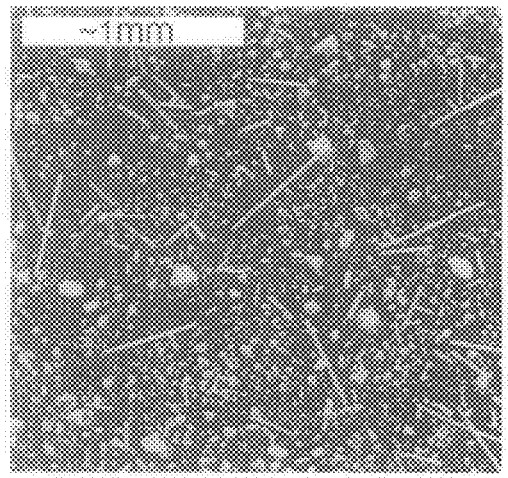
FIGS. 3A-3D are SEM images of a catalyst system 5% $Rh/Al_2O_3$ (sol-gel).
Figure 3B:
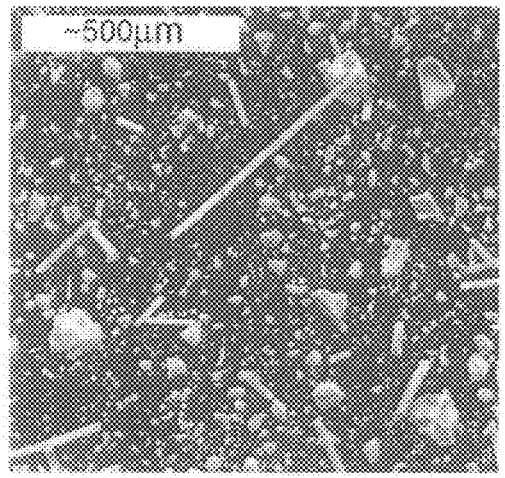
Figure 3C:
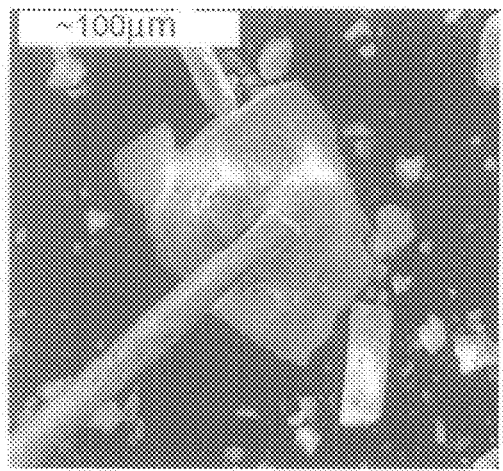
Figure 3D:
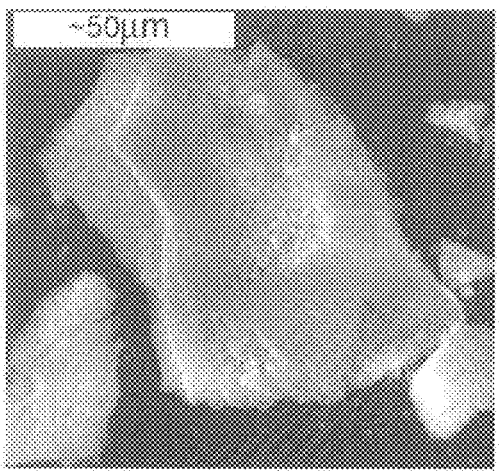

FIGS. 1 and 2 show the SEM images and EDX spectra for 5% $Rh/Al_2O_3$ catalyst. Specifically, FIG. 1A is an SEM image of fresh 5% $Rh/Al_2O_3$ sample. FIG. 1B is an SEM image of used 5% $Rh/Al_2O_3$ sample. FIG. 1C is an SEM image of fresh 5% $Rh/Al_2O_3$ sample, illustrating a detailed view of a particle. FIG. 1D is a detailed view of used 5% $Rh/Al_2O_3$ sample. The sample showed very fine irregular and coarse semi-spherical particles with long fibers. The particle size range was <10 to 150 μm. The particle surface close up views showed that it was composed of compacted fine particles of irregular shape. FIG. 2A is an EDX spectrum of a particle in 5% $Rh/Al_2O_3$ used sample. FIG. 2B is an EDX spectrum of fibers in 5% $Rh/Al_2O_3$ used sample. EDX analysis of particles showed the presence of Al, O and Rh. EDX analysis of fibers showed the presence of elements consistent with glass. Al and O, are expected of an alumina sample. Minor concentrations of C and Cl are also present. C is a common impurity found in alumina and is very difficult to remove. However, C will not affect Rh in such low concentrations.

5% $Rh/Al_2O_3$ (Sol Gel)

Figure 4A:
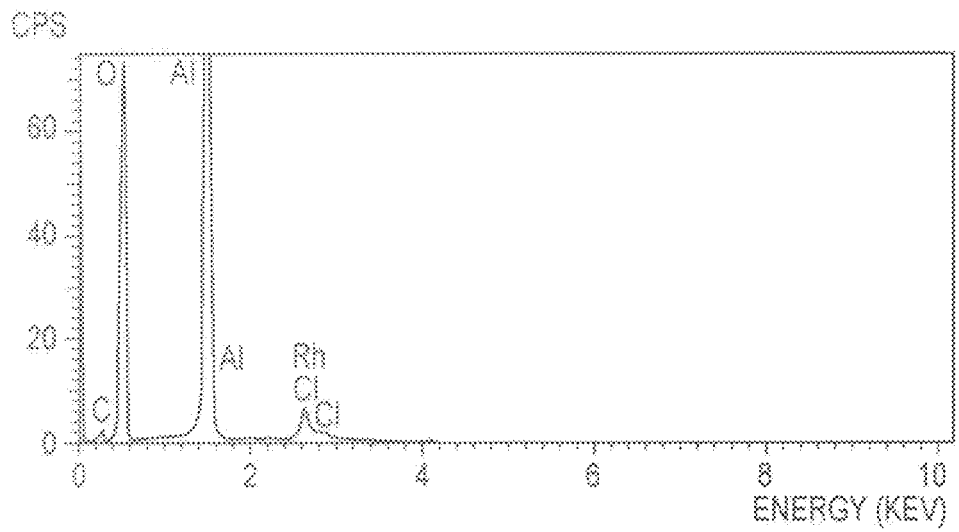
FIGS. 4A-4B are EDX spectra for 5% $Rh/Al_2O_3$ (sol-gel).
Figure 4B:
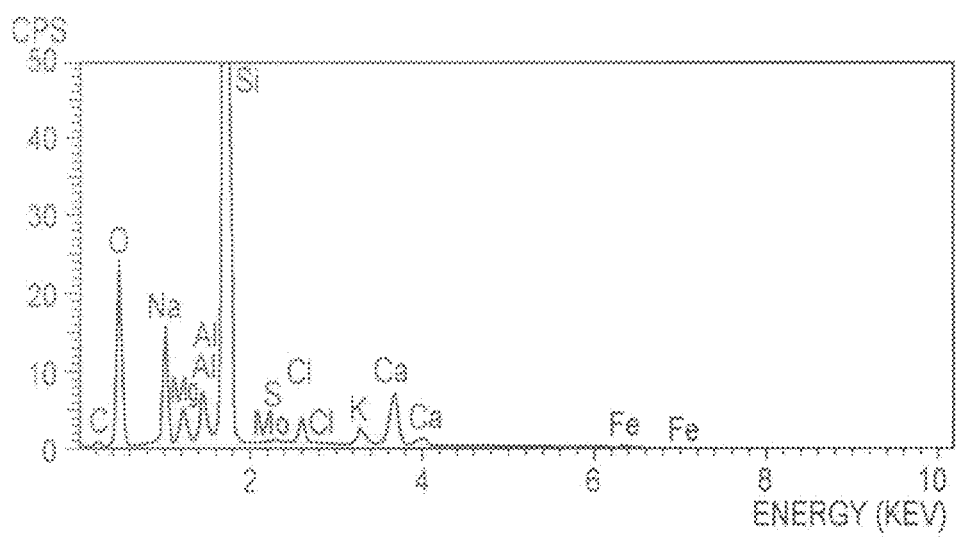
Figure 5A:
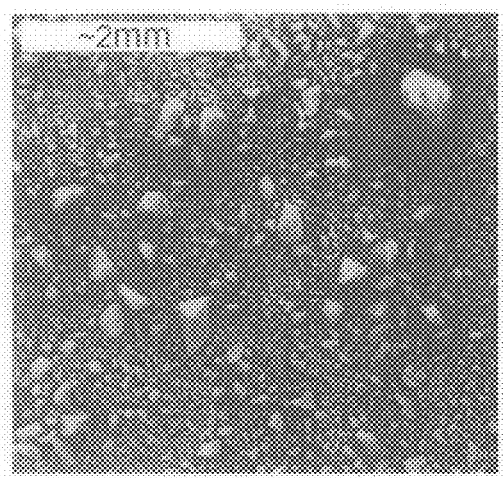
FIGS. 5A-5D are SEM images of a catalyst system 5% $Rh/SiO_2$.
Figure 5B:
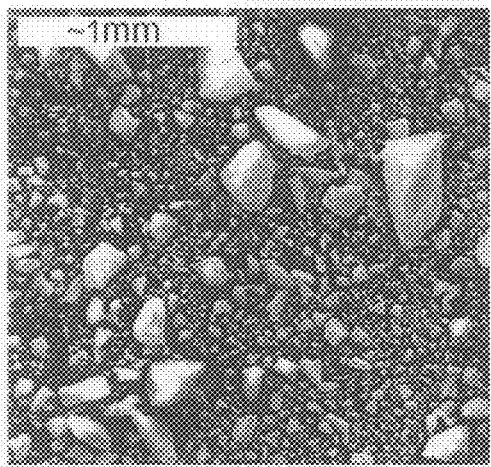
Figure 5C:
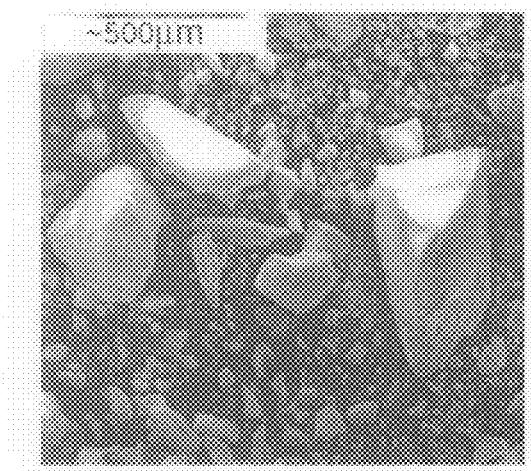
Figure 5D:
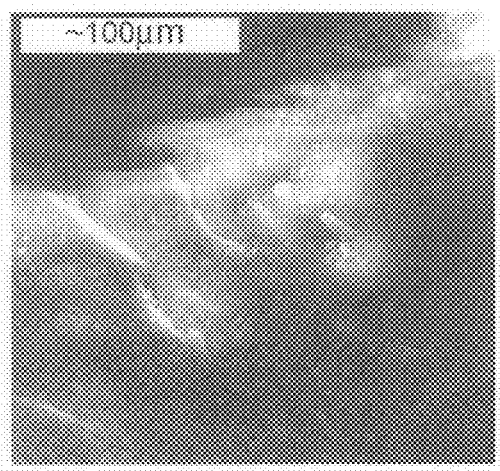

FIGS. 3 and 4 show the SEM images and EDX spectra for 5% $Rh/Al_2O_3$ (sol-gel) catalyst. Specifically, FIG. 3A is an SEM image of 5% $Rh/Al_2O_3$ (sol-gel). FIG. 3B is another SEM image of 5% $Rh/Al_2O_3$ (sol-gel). FIG. 3C is a detailed view of 5% $Rh/Al_2O_3$ (sol-gel) showing a particle and fiber. And, FIG. 3D is a detailed view of 5% $Rh/Al_2O_3$ (sol-gel) showing a particle. The catalyst showed very fine particles of irregular shape with high content of long fibers. The particle size range was <10 to 100 μm. The particle surface close up views showed the presence of fine particles and layer like structure especially in coarser particles. FIG. 4A is an EDX spectrum of a particle in 5% $Rh/Al_2O_3$ (sol-gel). FIG. 4B is an EDX spectrum of fibers in 5% $Rh/Al_2O_3$ (sol-gel). EDX analysis of fibers showed the presence of elements consistent with glass.

TABLE 1

Catalysts Characterization

| Sample | BET Surface Area ($m^2/g$) | Particle Size (Å) | CI wt (%) |
|---|---|---|---|
| 5% $Rh/Al_2O_3$ (fresh) | 135.5 | 247 | 1.2 |
| 5% $Rh/Al_2O_3$ (used) | 140.3 | 131 | 0.0 |
| 5% $Rh/Al_2O_3$ (sol gel) | 359.3 | 78.3 | 3.1 |
| 5% $Rh/SiO_2$ | 277.4 | 91.4 | 2.9 |
| 5% Rh/ZSM-5 | 283.8 | 14.8 | 4.4 |
| 5% Rh—20% $K/Al_2O_3$ | 48.5 | 161.7 | 4.8 |
| 52% $Ni/Al_2O_3$—$SiO_2$ | 228 | 96.9 | NA |
| 5% $Mo_2C/Al_2O_3$ | 97.4 | 143.6 | 0.0 |

5% $Rh/SiO_2$

Figure 6:
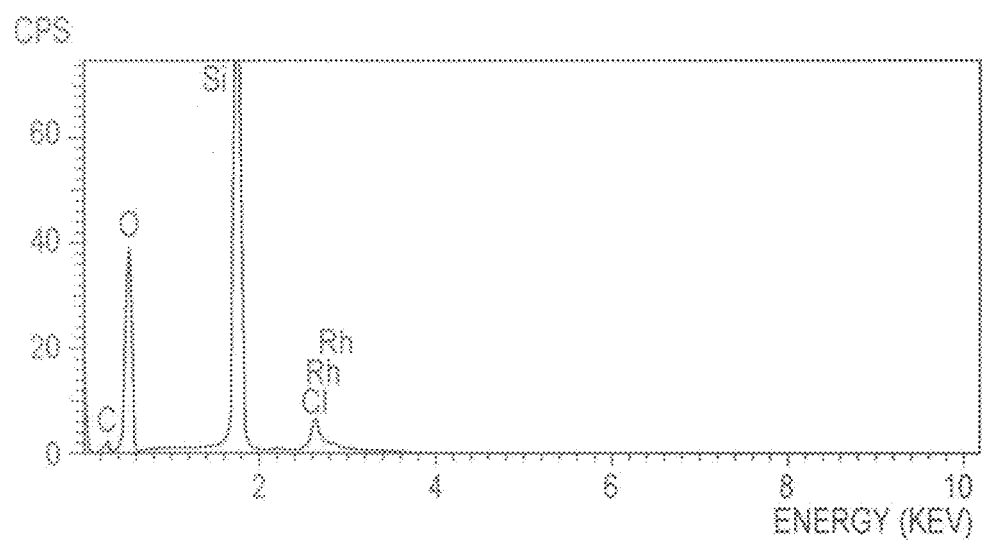
FIG. 6 is an EDX spectrum of a particle in 5% $Rh/SiO_2$.
Figure 7A:
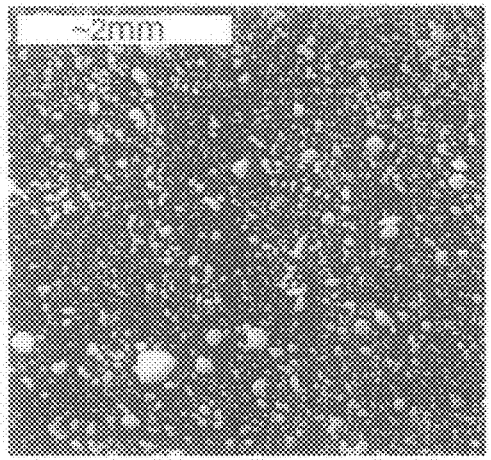
FIG. 7A-7D are SEM images of a catalyst system of 5% Rh/ZSM-5.
Figure 7B:
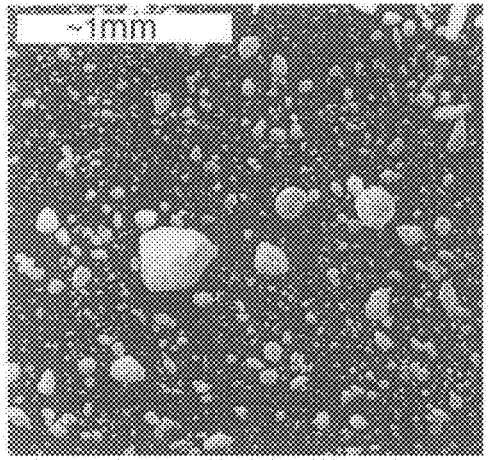
Figure 7C:
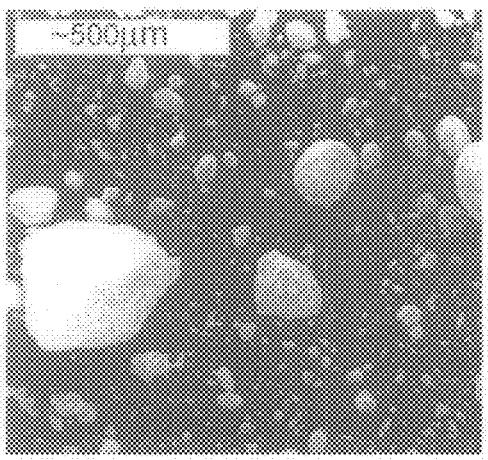
Figure 7D:
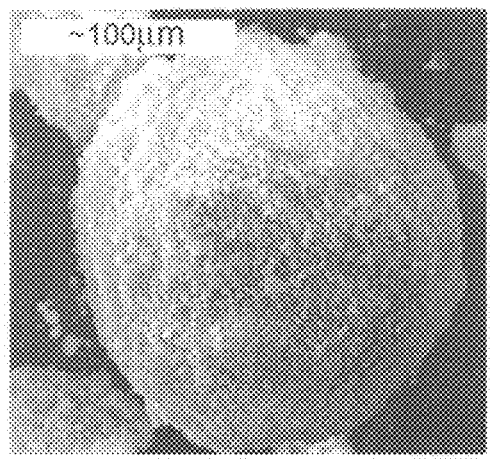

FIGS. 5 and 6 show the SEM images and EDX spectra for 5% $Rh/SiO_2$ catalyst. Specifically, FIG. 5A is an SEM image of 5% $Rh/SiO_2$. FIG. 5B is an SEM image of 5% $Rh/SiO_2$. FIG. 5C is a detailed view of a particle in 5% $Rh/SiO_2$, and, FIG. 5D is an SEM image of 5% $Rh/SiO_2$ showing a single particle. The sample showed sharp edged particles of irregular shape with variable size. The particle size range was <10 to 500 μm. The particle surface close up views showed the presence of fine surface particles. FIG. 6 is an EDX spectrum of a particle in 5% Rh/SiO$_2$. EDX analysis of particles showed the presence of Si, O, Cl and Rh.

5% Rh/ZSM-5

Figure 8:
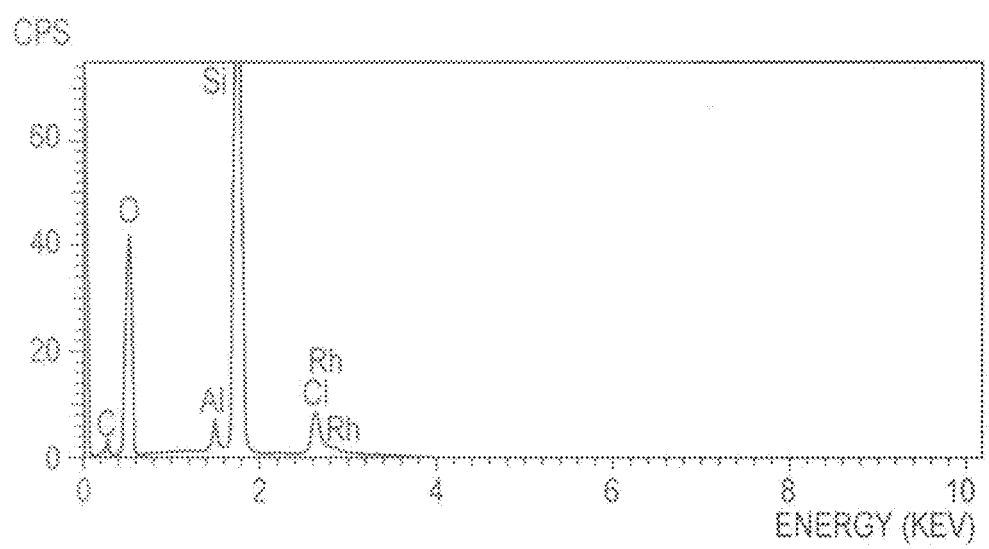
FIG. 8 is an EDX spectrum of a particle in 5% Rh/ZSM-5.
Figure 9A:
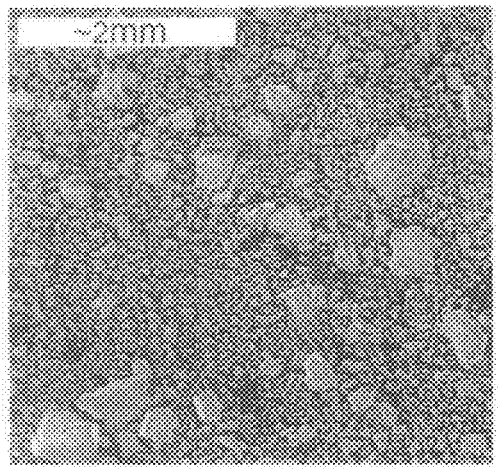
FIGS. 9A-9D are SEM images of a catalyst system of 5% Rh-20% $K/Al_2O_3$.
Figure 9B:
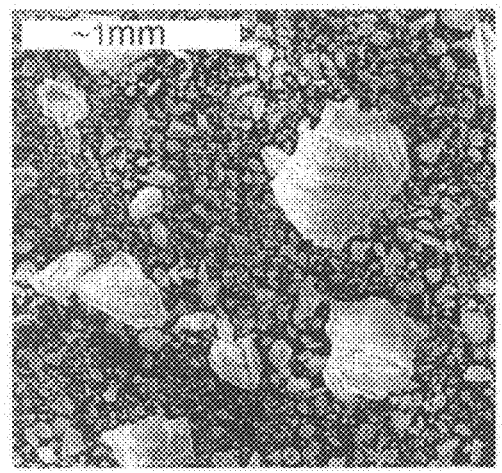
Figure 9C:
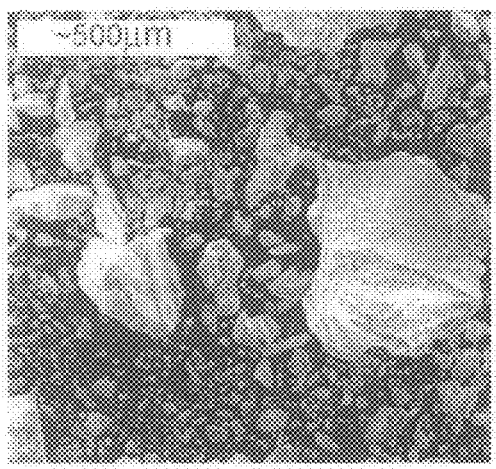
Figure 9D:
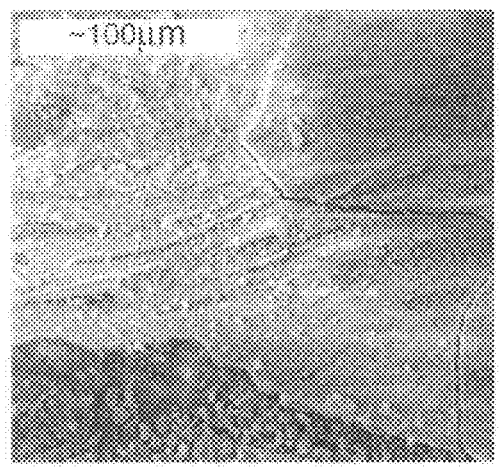

FIGS. 7 and 8 show the SEM images and EDX spectra for 5% Rh/ZSM-5 catalyst. Specifically, FIG. 7A is an SEM image of 5% Rh/ZSM-5. FIG. 7B is another SEM image of 5% Rh/ZSM-5. FIG. 7C is an SEM image of 5% RH/ZSM-5 illustrating a detailed view of particles, and, FIG. 7D is an SEM image of 5% Rh/ZSM-5 showing a detailed view of a single particle. The sample showed spherical and irregular round edged particles of variable size. The particle size range was <10 to 400 µm. The particle surface close up views showed the presence of high concentration of fine surface particles. FIG. 8 is an EDX spectrum of a particle in 5% Rh/ZSM-5. EDX analysis of particles showed the presence of Si, O, Al, Cl and Rh.

5% Rh-20% K/Al$_2$O$_3$

Figure 10:
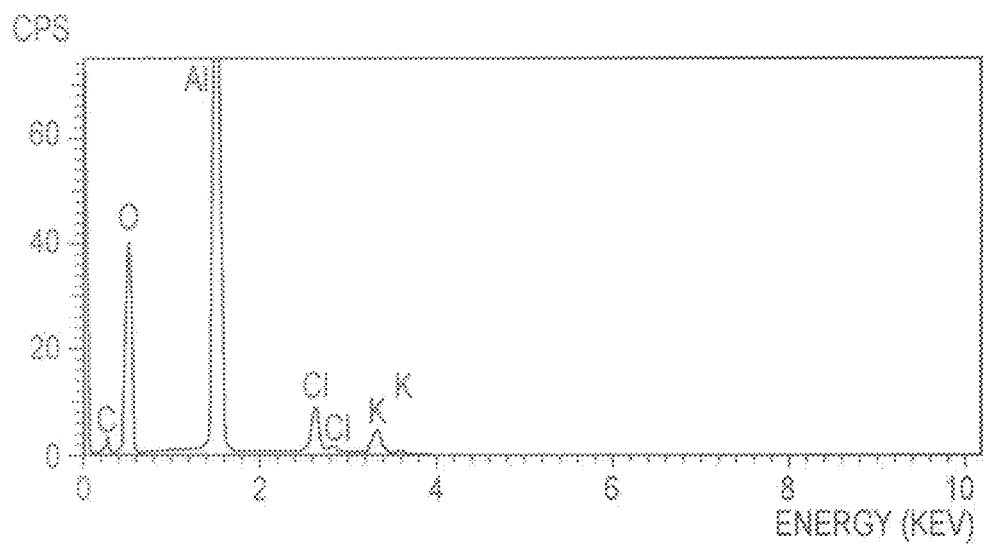
FIG. 10 is an EDX spectrum of a particle in 5% Rh-20% $K/Al_2O_3$.
Figure 11A:
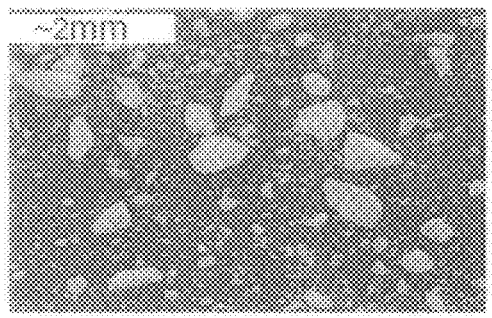
FIGS. 11A-11D are SEM images of a catalyst system of 52% $Ni/Al_2O_3$—$SiO_2$.
Figure 11B:
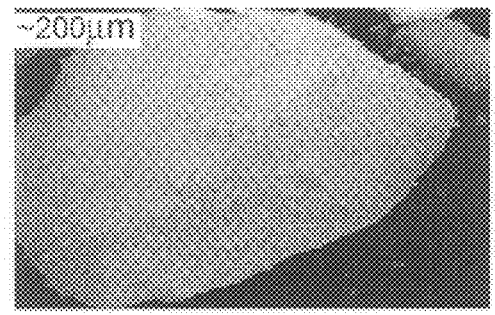
Figure 11C:
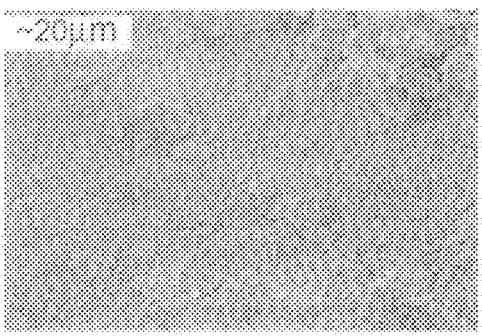
Figure 11D:
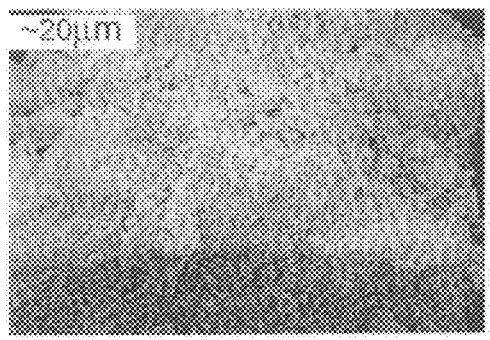
Figure 12A:
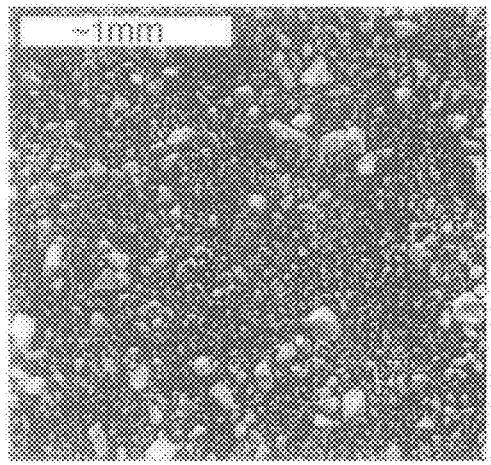
FIGS. 12A-12D are SEM images of a catalyst system of 5% $Mo_2C/Al_2O_3$.
Figure 12B:
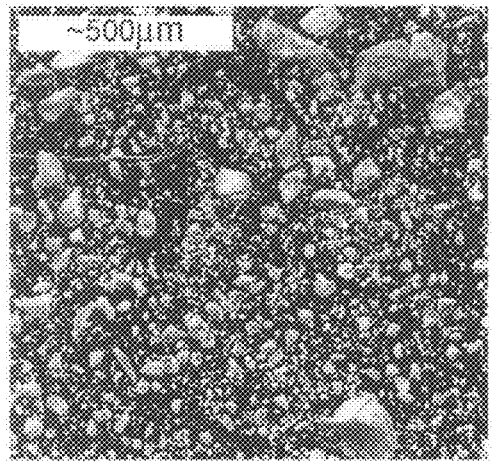
Figure 12C:
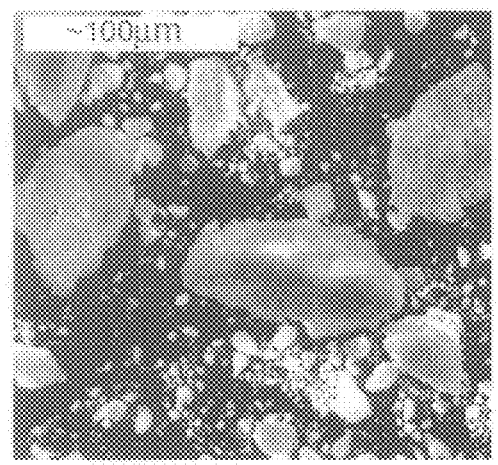
Figure 12D:
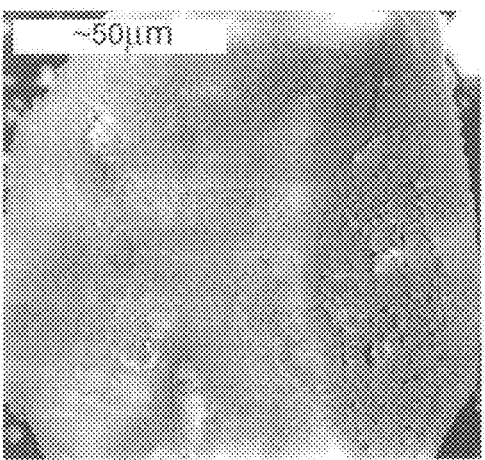

FIGS. 9 and 10 show the SEM images and EDX spectra for 5% Rh-20% K/Al$_2$O$_3$ catalyst. Specifically, FIG. 9A is an SEM image of 5% Rh-20% K/Al$_2$O$_3$. FIG. 9B is an SEM imaging showing individual particles in 5% Rh-20% K/Al$_2$O$_3$. FIG. 9C is an SEM image showing a detailed view of particles in 5% Rh-20% K/Al$_2$O$_3$. And, FIG. 9D is an SEM image of a single particle in 5% Rh-20% K/Al$_2$O$_3$. The sample showed sharp edged particles of irregular shape having variable sizes. The particle size range was <10 to 500 µm. The particle surface close up views showed the presence of fine surface particles and cracks. FIG. 10 is an EDX spectrum of particles in 5% Rh-20% K/Al$_2$O$_3$. EDX analysis of particles showed the presence of Al, O, Cl and K.

52% Ni/Al$_2$O$_3$—SiO$_2$

FIG. 11 shows the SEM images for 52% Ni/Al$_2$O$_3$—SiO$_2$ catalyst. Specifically, FIG. 11A is an SEM image of 52% Ni/Al$_2$O$_3$—SiO$_2$. FIG. 11B is a detailed view of a particle in 52% Ni/Al$_2$O$_3$—SiO$_2$. FIG. 11C is a further detailed view of a particle surface in 52% Ni/Al$_2$O$_3$—SiO$_2$, and, FIG. 11D is an SEM image of 52% Ni/Al$_2$O$_3$—SiO$_2$ further illustrating the particle surface. The sample was composed of sharp edged and irregular shaped particles having variable sizes. The close up views of individual particles showed that the particle surface contained agglomerated fine particles of variable sizes and shapes. The close up views of fine particles also showed the presence of similar morphology to that of coarser particles.

5% Mo$_2$C/Al$_2$O$_3$

Figure 13:
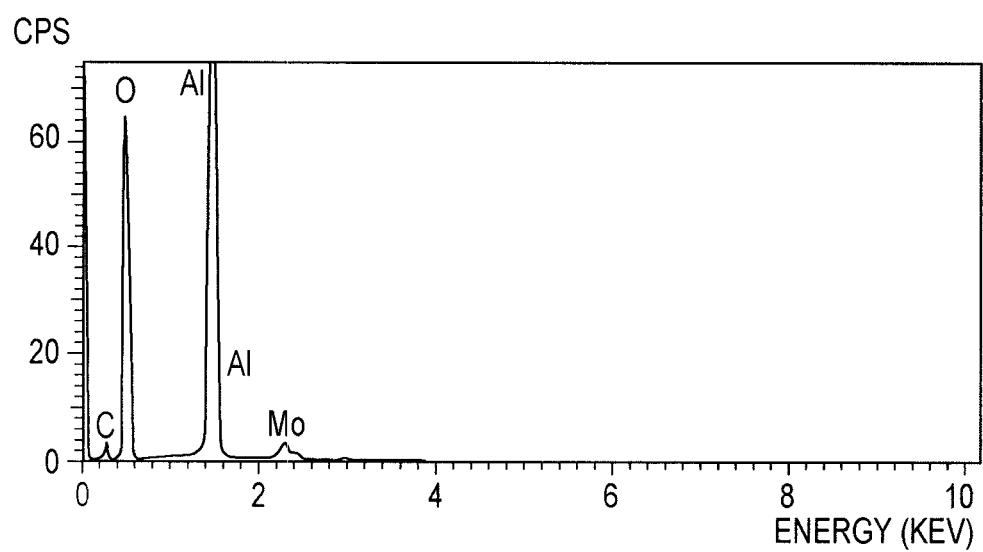
FIG. 13 is an EDX spectrum of a particle in 5% $Mo_2C/Al_2O_3$.

FIGS. 12 and 13 show the SEM images and EDX spectra for 5% Mo$_2$C/Al$_2$O$_3$ catalyst. Specifically, FIG. 12A is an SEM image of 5% Mo$_2$C/Al$_2$O$_3$. FIG. 12B is another SEM image of 5% Mo$_2$C/Al$_2$O$_3$. FIG. 12C is an SEM image of Mo$_2$C/Al$_2$O$_3$ illustrating a detailed view of a particle. And, FIG. 12 is an SEM image of a particle and its surface in 5% Mo$_2$C/Al$_2$O$_3$. The sample showed very fine particles of irregular shape with variable sizes. The particle size range was <10 to 250 µm. The particle surface close up views showed the presence of fine particles. FIG. 13 is an EDX spectrum of a particle in 5% Mo$_2$C/Al$_2$O$_3$. EDX analysis of particles showed the presence of Al, O and Mo.

A series of activity studies were conducted, as follows.

Rh—Containing Catalysts

5% Rh/Al$_2$O$_3$

Figure 14A:
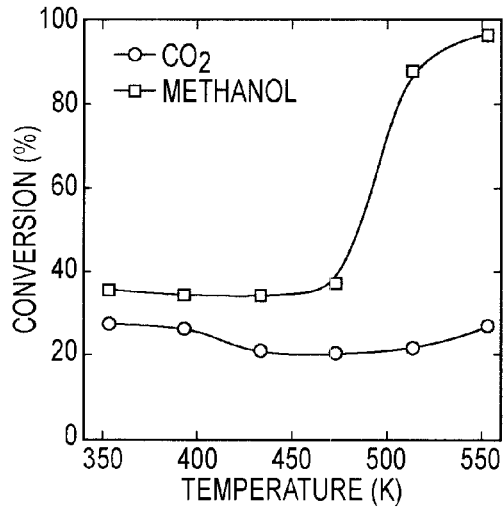
FIGS. 14A-14C are graphs illustrating the conversion of methanol, selectivity of DMC and formation rate of DMC, respectively, as a function of temperature using 5% $Rh/Al_2O_3$ catalyst.
Figure 14B:
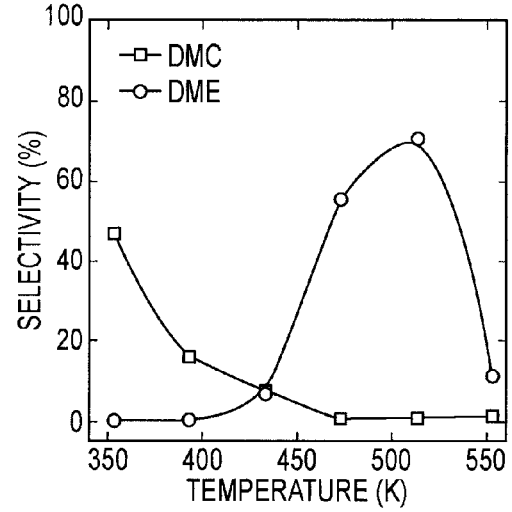
Figure 14C:
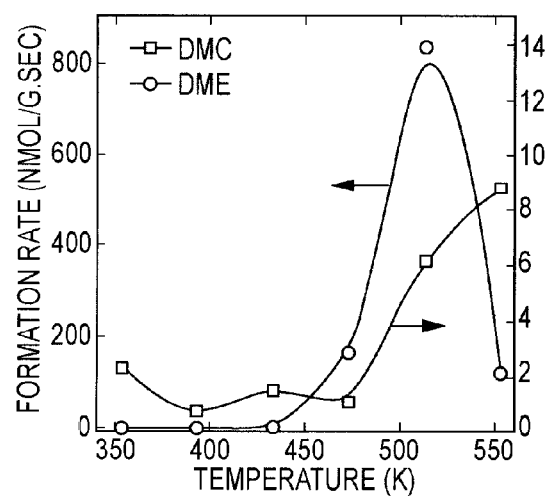

FIGS. 14A-14C show the conversion of methanol, selectivity of DMC, and formation rate of DMC, respectively, as a function of temperature during the reaction of methanol-CO$_2$ over 5% Rh/Al$_2$O$_3$ catalyst. The catalyst was prepared by incipient impregnation and had a surface area of 140.3 m$^2$ and a pore volume of 0.92 cm$^3$/g.

FIG. 14A shows that the conversion of methanol increases with temperature and that of CO$_2$ was almost constant. The unchanged conversion of CO$_2$ is due to its formation during the reaction. At 353 K (80° C.), the methanol conversion is as low as approximately 4%. With an increase in the temperature, the methanol conversion significantly rises from 14% to 95%, but at the same time undesirable reactions, i.e. decomposition of methanol, become dominant. A great quantity of CO appeared at 393 K (120° C.), which indicates that decomposition of methanol and CO$_2$ promoted by H-containing compounds also occurs on the surface, thus hindering the DMC formation. The methanol conversion reaches a maximum (98%) at 553 K (280° C.). The increase in the methanol conversion was accompanied by a decrease in the DMC selectivity, an increase in that of dimethyl ether (DME), and an increase in the formation rate of DMC as shown in FIGS. 14B and 14C, respectively.

At temperatures higher than 400 K (127° C.), the DMC selectivity and yield was far from satisfactory. Weak acidity is very important in the selective DMC synthesis since the expectable by-product DME is easily formed on the rather strong acid sites. When DME is formed together with H$_2$O, no DMC was observed due to the more favorable hydrolysis reaction of DMC.

Evidently, the results shown in FIGS. 14A-14C demonstrate that: (i) low temperature is more favorable for DMC formation and this is because the reaction is exothermic, (ii) DMC synthesis from methanol and CO$_2$ is a reversible reaction, and (iii) DMC selectivity is limited by the equilibrium of (reaction XII), which shifts the reaction to the left to avoid the formation of water.

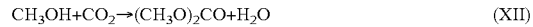

$$CH_3OH + CO_2 \rightarrow (CH_3O)_2CO + H_2O \quad (XII)$$

Water produced during the reaction can react further with methanol to produce CO$_2$ and H$_2$ likely via the reforming reaction of methanol (reaction XIII).

$$CH_3OH + H_2O \rightarrow CO_2 + 3H_2 \quad (XIII)$$

Removal of water from the reaction system by circulating the reaction mixture through a dehydrating tube enhanced the methanol conversion and DMC selectivity at high temperatures. DMC decomposition and methanol dehydration to DME represents a major loss of the DMC selectivity.

5% Rh/Al$_2$O$_3$ (Sol-Gel)

Figure 15A:
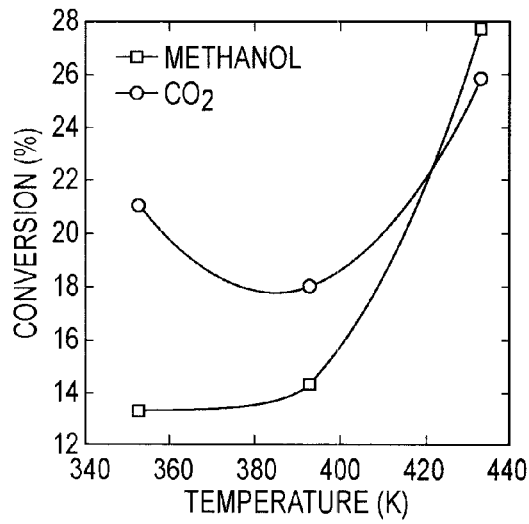
FIGS. 15A-15C are graphs illustrating the conversion of methanol, selectivity of DMC, and formation rate of DMC, respectively, as a function of temperature using 5% $Rh/Al_2O_3$ (sol-gel) catalyst.
Figure 15B:
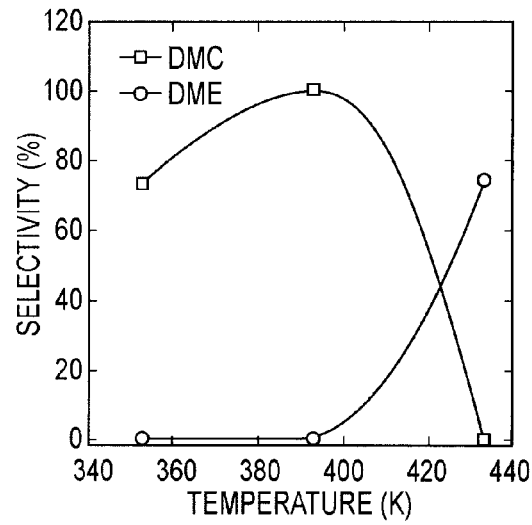
Figure 15C:
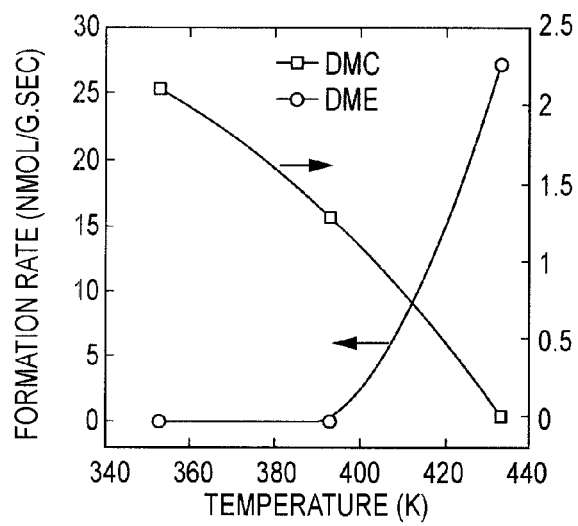

FIGS. 15A-15C show the conversion of methanol, selectivity of DMC, and formation rate of DMC as a function of temperature during the reaction of methanol/CO$_2$ over 5% Rh/Al$_2$O$_3$ (sol-gel) catalyst. The catalyst was prepared by sol-gel method and had a surface area of 359.3 m$^2$ and a pore volume of 1.41 cm$^3$/g. It was reported that an alumina support synthesized through a sol-gel method has superior properties, such as high purity and homogeneity at a molecular scale and well controlled acidic and basic sites.

The methanol conversion and DMC selectivity at low temperature were 15% and 100%, respectively. The DME formation escalated at 433 K (160° C.) while that of DMC was decreasing. The difference between this catalyst and that prepared by impregnation, i.e. FIGS. 14A to 14C, is the earlier formation of DME on Rh/Al$_2$O$_3$ (sol-gel) at 440 K (167° C.) (25 nmol/g·sec) as compared to 473 K (200° C.) over Rh/Al$_2$O$_3$.

5% Rh/SiO$_2$

Figure 16A:
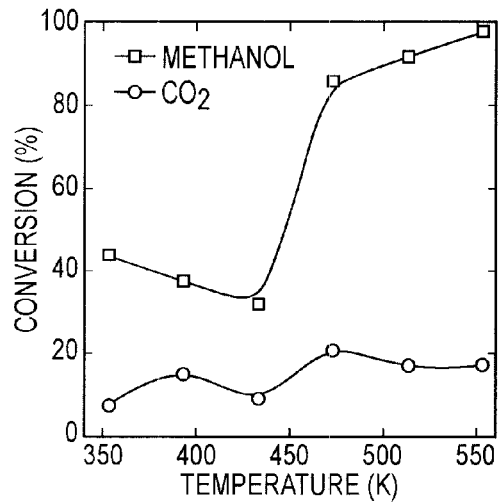
FIGS. 16A-16C are graphs illustrating the conversion of methanol, selectivity of DMC, and formation rate of DMC, respectively, as a function of temperature using 5% $Rh/SiO_2$ (sol-gel) catalyst.
Figure 16B:
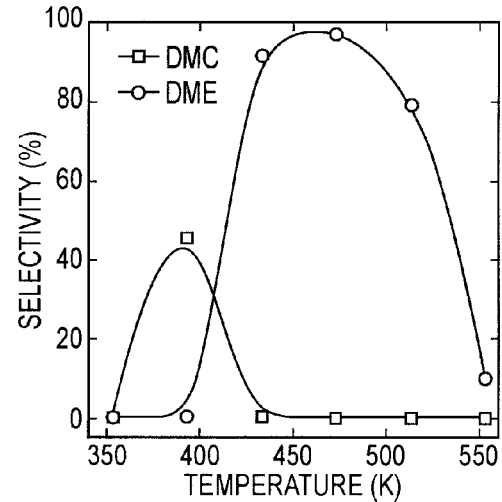
Figure 16C:
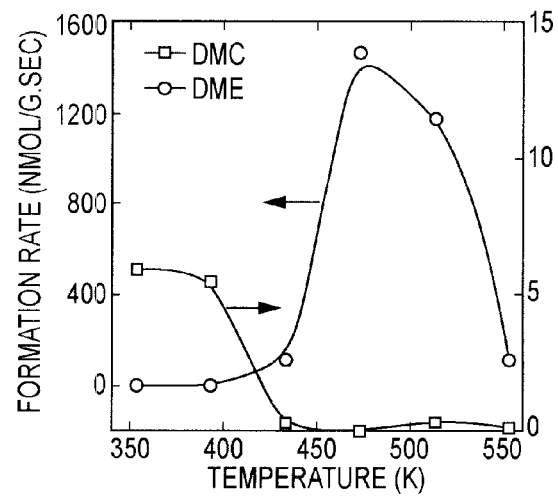

FIGS. 16A-16C show the conversion of methanol, selectivity of DMC, and formation rate of DMC as a function of temperature during the reaction of methanol-CO$_2$ over 5% Rh/SiO$_2$ catalyst. The catalyst had a surface area of 277.4 m$^2$. The methanol conversion decreases with temperature while DMC selectivity increased and reached 40% level at 393 K (120° C.). However, DME selectivity reached 100% at 473 K (200° C.).

5% Rh/ZSM-5

Figure 17A:
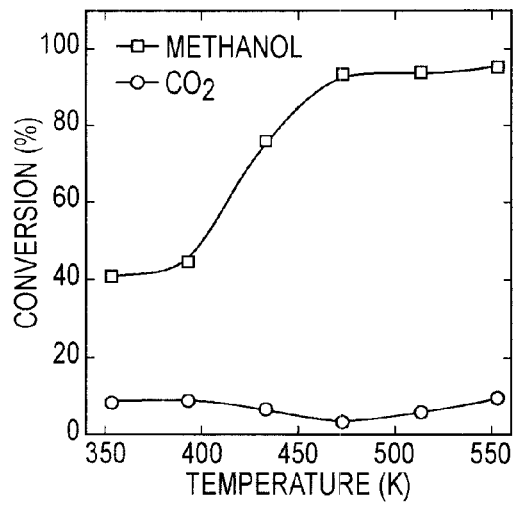
FIGS. 17A-17C are graphs illustrating the conversion of methanol, selectively of DMC, and formation rate of DMC, respectively, as a function of temperature using 5% Rh/ZSM-5 catalyst.
Figure 17B:
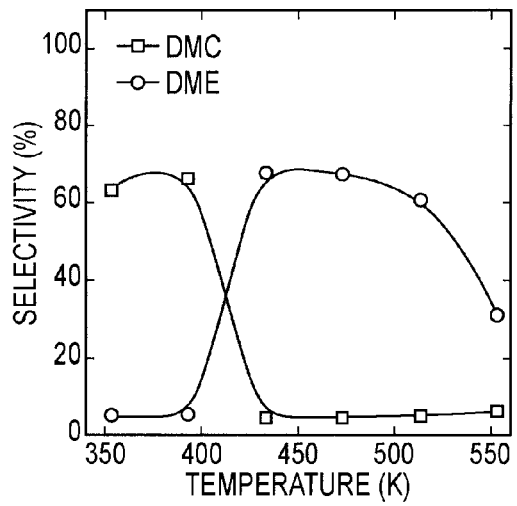
Figure 17C:
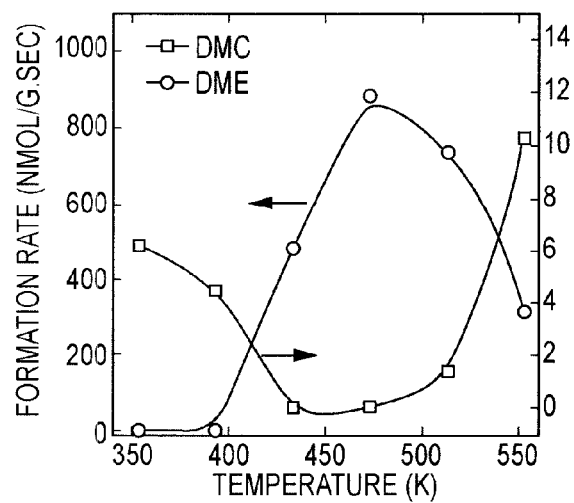

FIGS. 17A-17C show the conversion of methanol, selectivity of DMC, and formation rate of DMC as a function of temperature during the reaction of methanol/$CO_2$ over 5% Rh/ZSM-5 catalyst. The catalyst had a surface area of 283.8 $m^2$. The methanol conversion increased continuously and reached 98% at 473 K (200° C.). The highest DMC selectivity obtained was 63% at 393 K (120° C.) and that of DME was 62% in the range 433-513 K (160-240° C.) (as shown in FIG. 17B). The formation rate of DMC was 6 nmol/g·sec at 353-373 K (80-100° C.), while the DME formation rate was zero at 373 K (100° C.) (as shown in FIG. 17C).

5% Rh-20% K/$Al_2O_3$

Figure 18A:
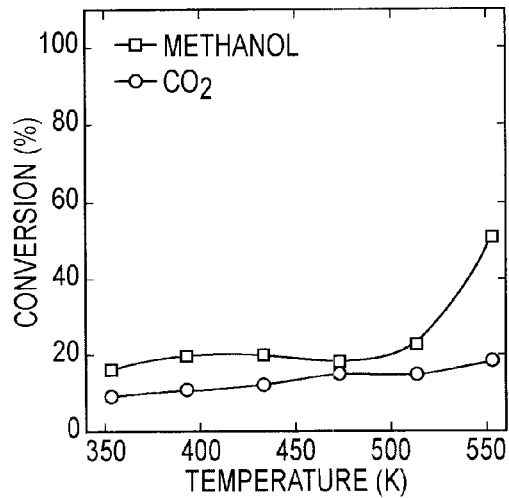
FIGS. 18A-18C are graphs illustrating the conversion of methanol, selectivity of DMC, and formation rate of DMC, respectively, as a function of temperature using 5% Rh-20% $K/Al_2O_3$ catalyst.
Figure 18B:
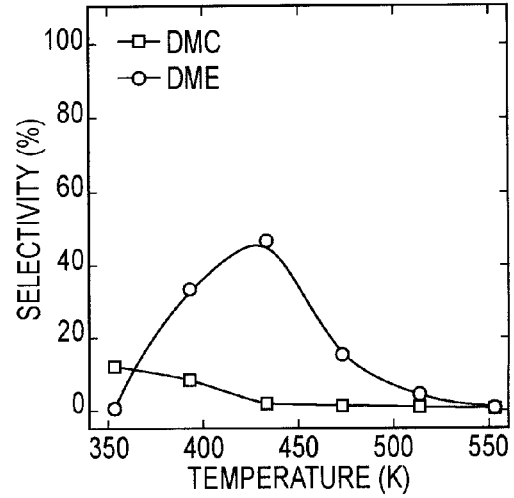
Figure 18C:
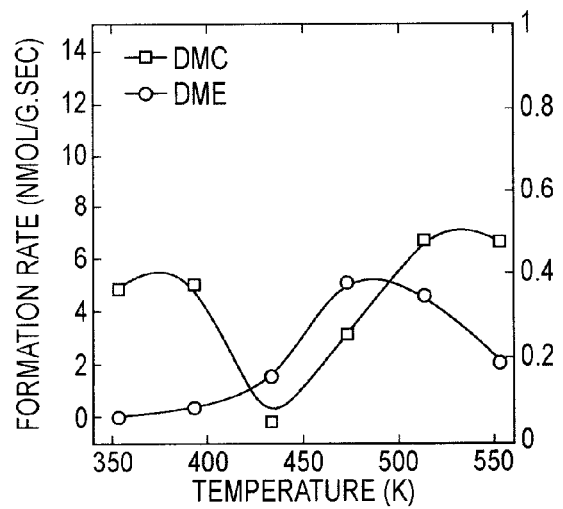
Figure 19A:
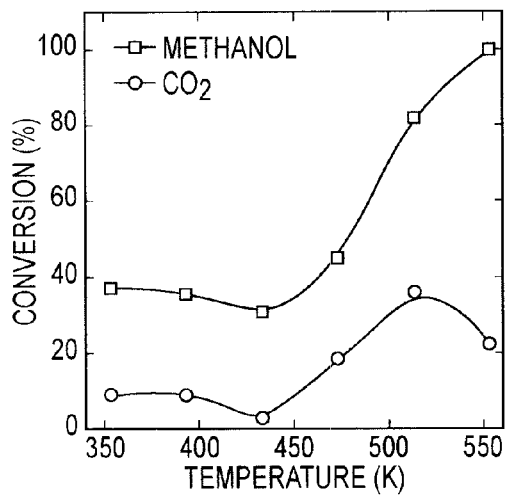
FIGS. 19A-19C are graphs illustrating the conversion of methanol, selectivity of DMC, and formation rate of DMC, respectively, as a function of temperature using 5% Rh-20% $Ce/Al_2O_3$ catalyst.
Figure 19B:
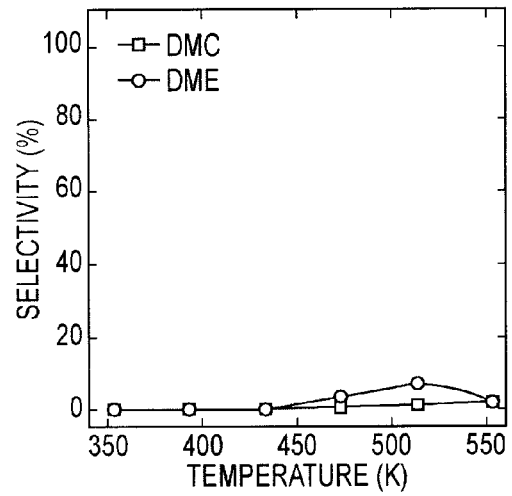
Figure 19C:
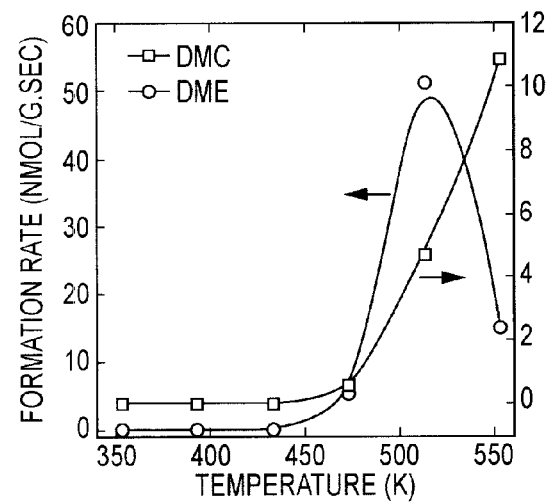
Figure 20A:
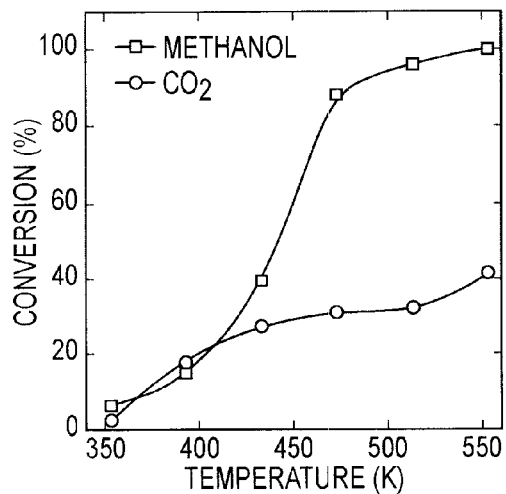
FIGS. 20A-20C are graphs illustrating the conversion of methanol, selectively of DMC, and formation rate of DMC, respectively, as a function of temperature using 5% Rh-20% Ni/ZSM-5 catalyst.
Figure 20B:
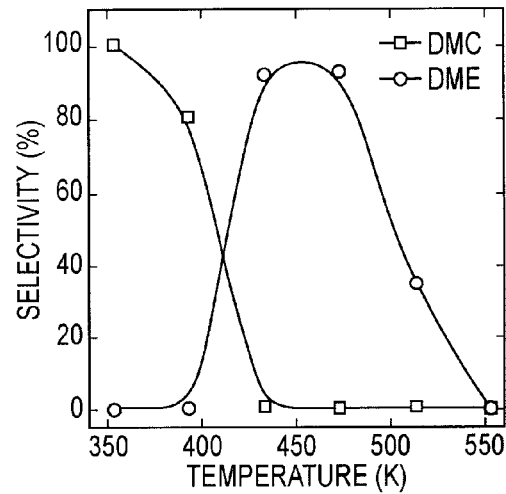
Figure 20C:
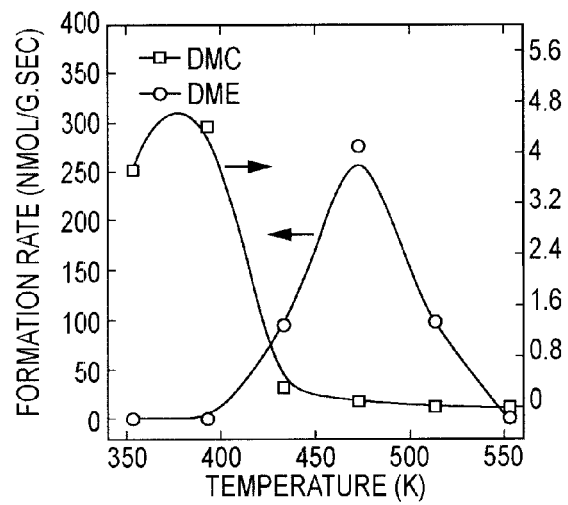

FIGS. 18A-18C show the conversion of methanol, selectivity of DMC, and formation rate of DMC as a function of temperature during the reaction of methanol/$CO_2$ over 5% Rh-20% K/$Al_2O_3$ catalyst. The catalyst had a surface area of 48.5 $m^2$. Addition of K as a promoter to Rh/$Al_2O_3$ catalyst had a negative effect on the methanol conversion and DMC selectivity. Similar effects occurred when Ce or Ni were added to Rh-supported catalysts (as shown in FIGS. 19 and 20). These effects were due to a decrease in the surface area (as shown in Table 1) and dilution of the Rh sites by K, Ce, or Ni. However, it will be appreciated that in certain applications, it may be desirable to incorporate one or more of these promoters in a heterogeneous catalyst.

Sol-Gel Catalysts

Figure 21A:
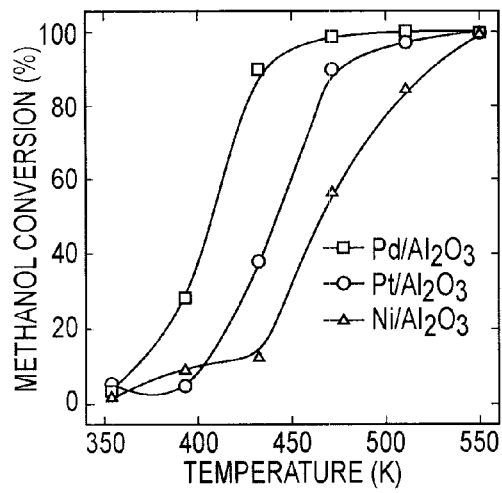
FIGS. 21A-21C are graphs illustrating the conversion of methanol, selectively of DMC, and formation rate of DMC, respectively, as a function of temperature using sol-gel catalyst.
Figure 21B:
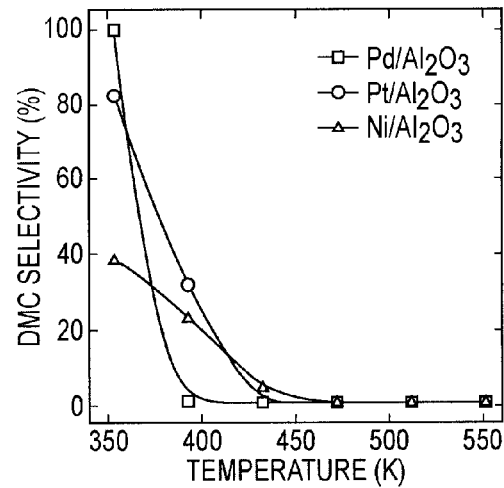
Figure 21C:
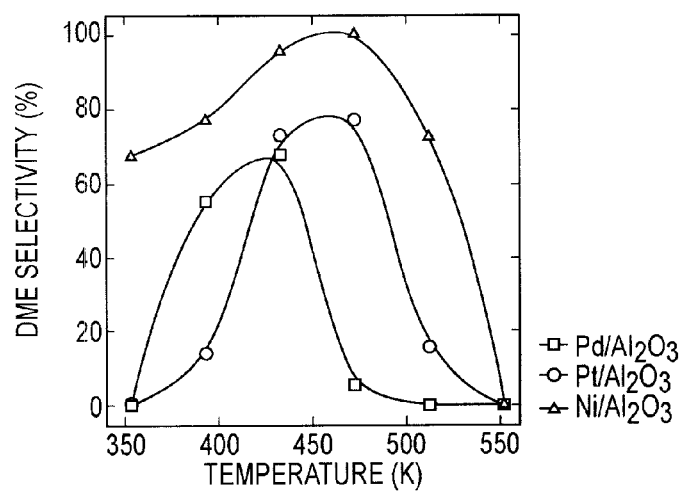

FIGS. 21A-21C show the conversion of methanol, selectivity of DMC, and formation rate of DMC as a function of temperature during the reaction of methanol-$CO_2$ over catalysts prepared by sol-gel method. The results were similar to those catalysts of Rh prepared by wetness impregnation method where DMC was formed at a low temperature and methanol conversion. The methanol light-off temperature, i.e. the temperature at which 50% conversion was achieved, was Pd=407 K (134° C.), Pt=443 K (170° C.), Ni=466 K (193° C.) indicating that Pd was the most active catalyst as compared to Pt and Ni. The Pd catalyst shows better DMC selectivity (the DMC selectivity decreased in the following order: Pd>Pt>Ni). Ni catalyst showed high selectivity towards DME as compared to Pd and Pt. The sol-gel method was used to give well defined surface acidity/basicity. The surface area and pore volume were higher for those catalysts prepared by sol-gel method as compared to those prepared by an impregnation method.

$Mo_2$-Containing Catalysts

5% $Mo_2C/Al_2O_3$

Figure 22A:
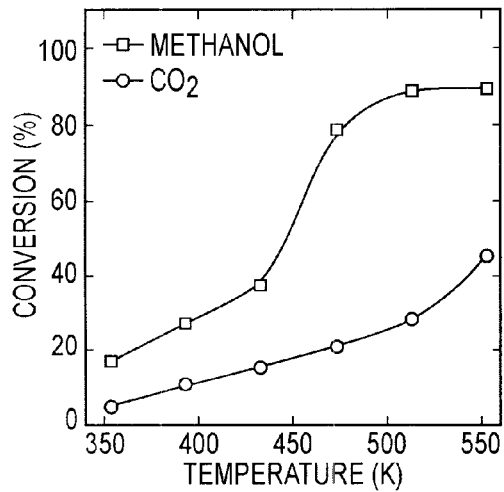
FIGS. 22A-22C are graphs illustrating the conversion of methanol, selectivity of DMC, and formation rate of DMC, respectively, as a function of temperature using 5% $Mo_2C/Al_2O_3$ catalyst.
Figure 22B:
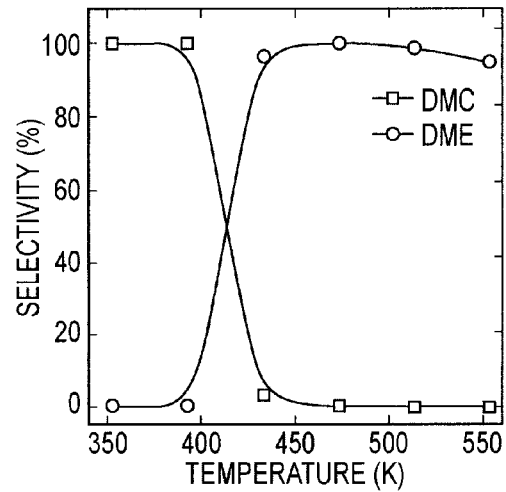
Figure 22C:
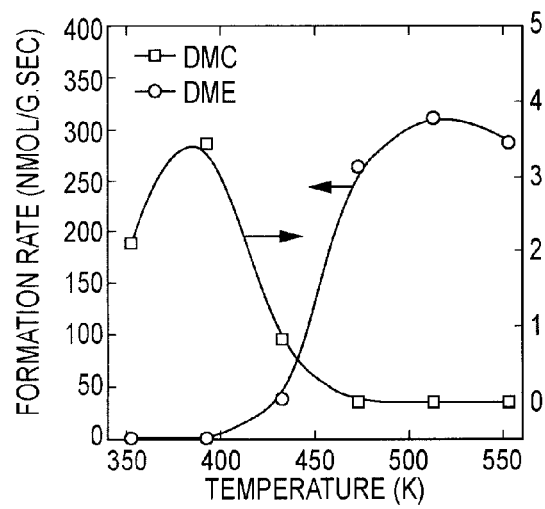

FIGS. 22A-22C show the conversion of methanol, selectivity of DMC, and formation rate of DMC as a function of temperature during the reaction of methanol-$CO_2$ over 5% $Mo_2C/Al_2O_3$ catalyst. The catalyst had a surface area of 97.4 $m^2$. Over this catalyst, the DMC formed with a selectivity of 100% between 353 K (80° C.) and 393 K (120° C.), while on Rh/$Al_2O_3$ it was only 55% at 353 K (80° C.). On this catalyst, 433K (160° C.) proved to be the threshold temperature, where DME production is dominant as in the case of Rh. At higher temperatures (513 K (240° C.) to 553 K (280° C.)), hydrogen, CO, methane, and ethane were produced as a result of the decomposition of methanol and $CO_2$.

Figure 23A:
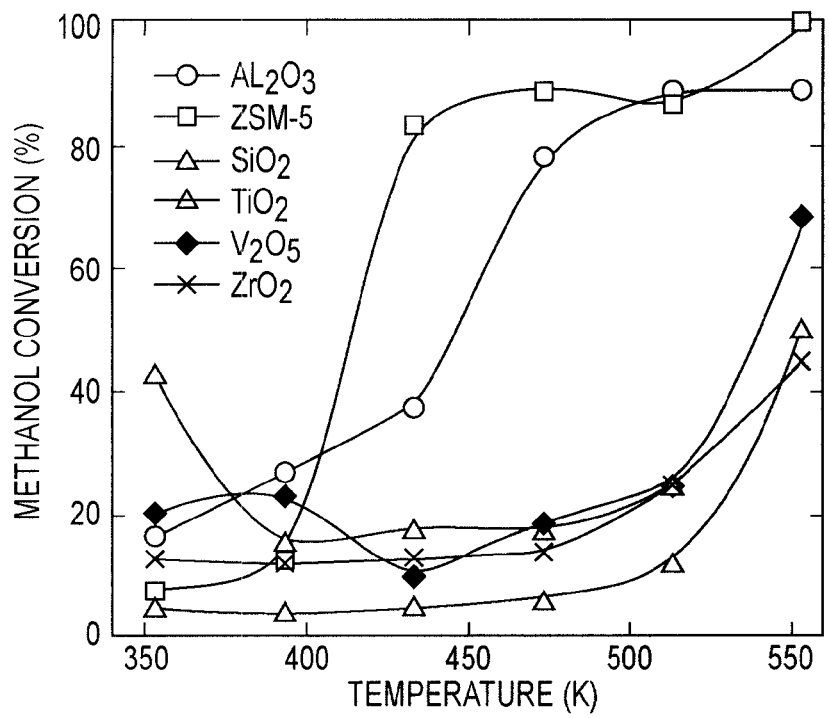
FIGS. 23A-23B are graphs illustrating the conversion of methanol and the selectivity of DMC as a function of temperature using supported $Mo_2C$ catalysts.
Figure 23B:
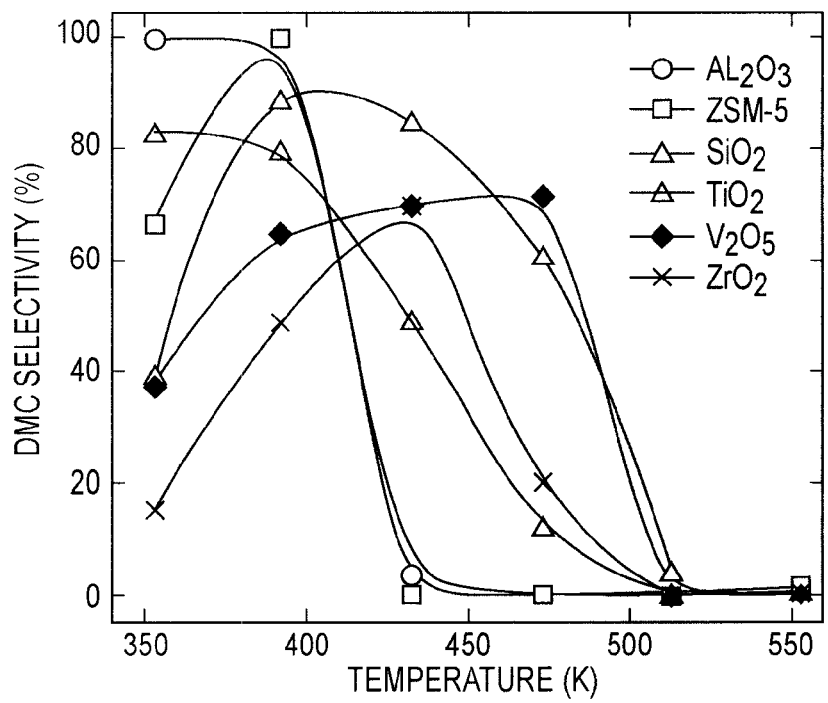

FIGS. 23A-23B show the effect of support on the conversion of methanol and selectivity of DMC, as a function of temperature during the reaction of methanol-$CO_2$ over supported $Mo_2C$ catalysts. It was found that DMC selectivity did not reach 100% even at 353-393 K (80-120° C.) on all supports with the exception of $Al_2O_3$ and ZSM-5. When $ZrO_2$ and $V_2O_5$ were used as supports, DMC selectivity increased to a small extent with the rise of the temperature and was not accompanied by an increase in methanol conversion. The DMC yield (Y) was in the following order: $Y_{Al2O3}$=27, $Y_{SiO2}$=15.2, $Y_{V2O5}$=13.8, $Y_{ZSM-5}$=11, $Y_{ZrO2}$=4.7, $Y_{TiO2}$=2.4. This indicates that the support greatly affects the DMC selectivity through the stabilization of surface methoxy groups in the environment of adsorbed $CO_2$.

Figure 24A:
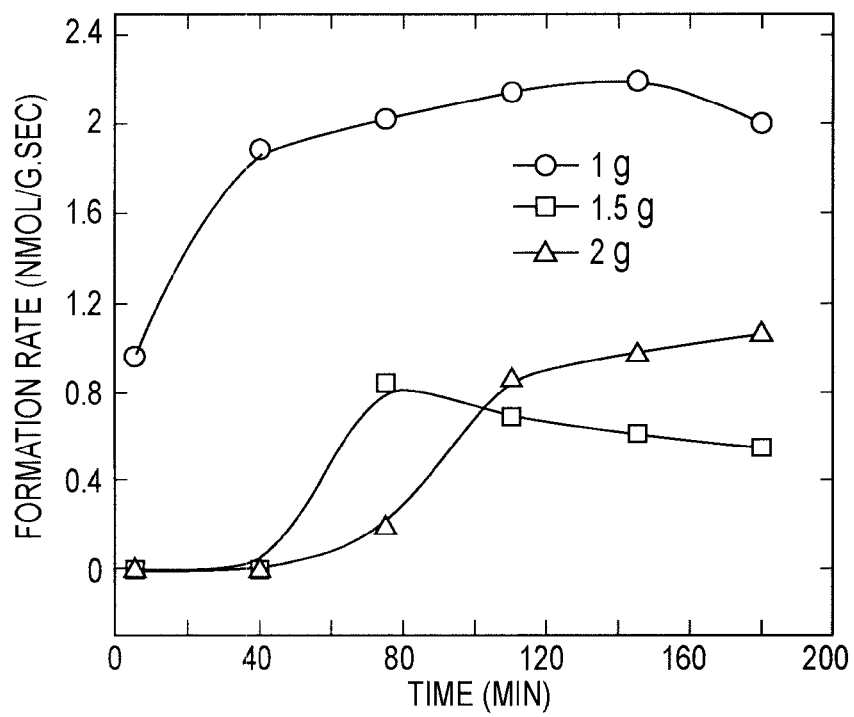
FIGS. 24A-24B are graphs illustrating DMC formation rate over 5% $Mo_2C/Al_2O_3$ for different catalyst weights and different reactant ratios.
Figure 24B:
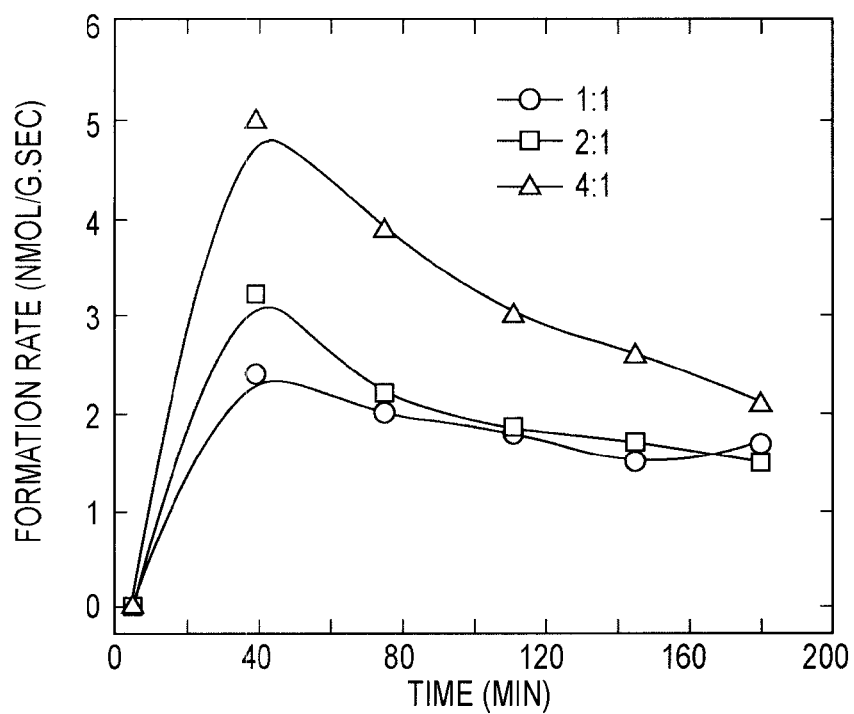
Figure 25A:
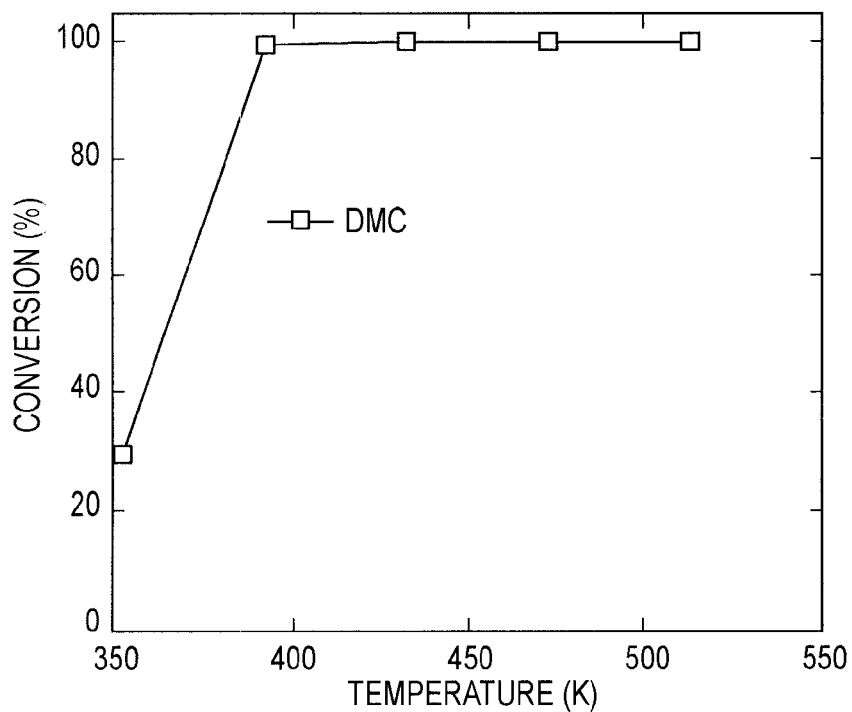
FIGS. 25A-25B are graphs illustrating DMC decomposition over 5% $Mo_2C/Al_2O_3$ at different temperatures.
Figure 25B:
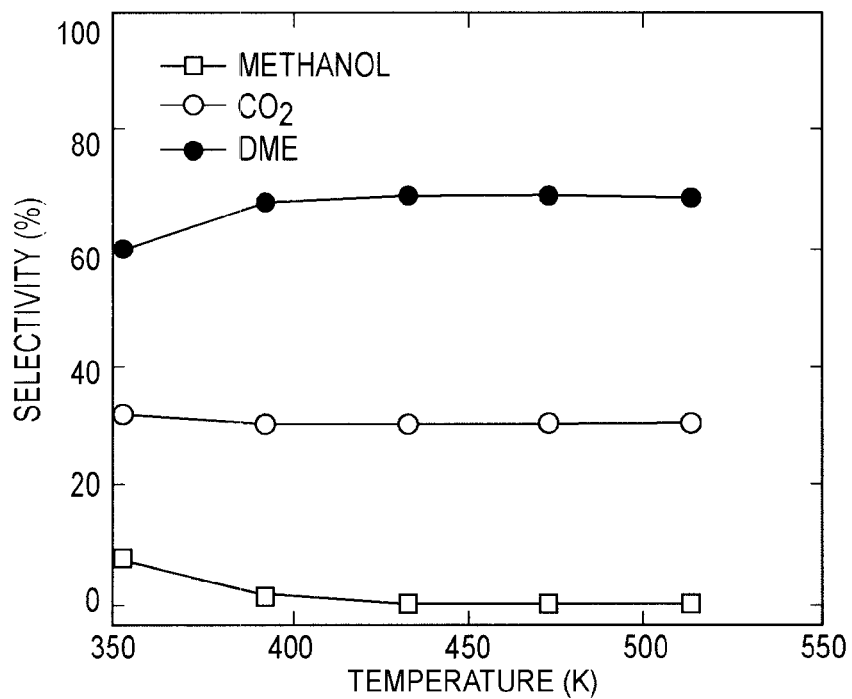

FIGS. 24A-24B show the effects of catalyst weight and reactants ratio on the DMC formation rate during the reaction of methanol-$CO_2$ over 5% $Mo_2C/Al_2O_3$ catalyst at 393 K (120° C.). The rate of DMC formation decreased from 3.3 nmol/g·sec at 0.5 g to 0.9 nmol/g·sec at 2 g. This may indicate that on a relatively large quantity of the catalyst, the decomposition of DMC becomes more dominant. This is clearly demonstrated following the decomposition of DMC over 5% $Mo_2C/Al_2O_3$ (FIGS. 25A-25B). It has been reported that the DMC decomposition is the main reason of the decrease of DMC formation at high temperature. The activation energy of DMC decomposition is lower than that of the reaction of methanol and $CO_2$ at the given conditions.

In yet another series of investigations, conversion of methanol and formation and selectivity of DMC was investigated for various Pd-containing catalysts, Re-containing catalysts, and $MoO_3$-containing catalysts. The results of these investigations are set forth below in Tables 2 to 11.

TABLE 2

DMC Formation Using 5% Pd/$V_2O_5$

| Temperature (° C.) | DMC Selectivity (%) | DMC Formation rate [nmol/gsec] | Methanol conversion (%) |
|---|---|---|---|
| 80 | 100 | 0.26 | 12.00 |
| 120 | 48 | 1.70 | 13.00 |
| 160 | 12 | 0.70 | 18.00 |
| 200 | 0 | 0 | 65.00 |
| 240 | 0 | 0 | 66 |
| 280 | 0 | 0 | 99 |

TABLE 3

DMC Formation Using 5% Pd/$TiO_2$

| Temperature (° C.) | DMC Selectivity (%) | DMC Formation rate [nmol/gsec] | Methanol conversion (%) |
|---|---|---|---|
| 80 | 100 | 0.56 | 9.00 |
| 120 | 4 | 0.33 | 11.00 |
| 160 | 0 | 0 | 20.00 |
| 200 | 0 | 0 | 68.00 |
| 240 | 0 | 0 | 98 |
| 280 | 0 | 0 | 99 |

TABLE 4

DMC Formation Using 5% Pd/$TiO_2$—$V_2O_5$

| Temperature (° C.) | DMC Selectivity (%) | DMC Formation rate [nmol/gsec] | Methanol conversion (%) |
|---|---|---|---|
| 80 | 76 | 0.7 | 2.00 |
| 120 | 0 | 0 | 4.00 |
| 160 | 0 | 0 | 21.00 |
| 200 | 0 | 0 | 70.00 |
| 240 | 0 | 0 | 96 |
| 280 | 0 | 0 | 98 |

TABLE 5

DMC Formation Using 5% Pd/TiO$_2$—ZrO$_2$

| Temperature (° C.) | DMC Selectivity (%) | DMC Formation rate [nmol/gsec] | Methanol conversion (%) |
|---|---|---|---|
| 80 | 50 | 0.60 | 3.00 |
| 120 | 38 | 1.40 | 5.00 |
| 160 | 6 | 0.00 | 8.00 |
| 200 | 0 | 0 | 15.00 |
| 240 | 0 | 0 | 56 |
| 280 | 0 | 0 | 97 |

TABLE 6

DMC Formation Using 5% Re/Al$_2$O$_3$

| Temperature (° C.) | DMC Selectivity (%) | DMC Formation rate [nmol/gsec] | Methanol conversion (%) |
|---|---|---|---|
| 80 | 35 | 0.60 | 11.00 |
| 120 | 100 | 1.40 | 13.00 |
| 160 | 3 | 0.00 | 16.00 |
| 200 | 0 | 0 | 81.00 |
| 240 | 0 | 0 | 92 |
| 280 | 0 | 0 | 97 |

TABLE 7

DMC Formation Using 5% MoO$_3$/Al$_2$O$_3$

| Temperature (° C.) | DMC Selectivity (%) | DMC Formation rate [nmol/gsec] | Methanol conversion (%) |
|---|---|---|---|
| 80 | 100 | 0.22 | 2.00 |
| 120 | 100 | 2.2 | 4.00 |
| 160 | 30 | 6 | 15.00 |
| 200 | 0.15 | 0.18 | 62.00 |
| 240 | 0 | 0 | 85 |
| 280 | 0 | 0 | 85 |

TABLE 8

DMC Formation Using 5% MoO$_3$/ZSM-5 (SiO$_2$:Al$_2$O$_3$ = 30)

| Temperature (° C.) | DMC Selectivity (%) | DMC Formation rate [nmol/gsec] | Methanol conversion (%) |
|---|---|---|---|
| 80 | 0 | 0.00 | 7.00 |
| 120 | 7 | 1.50 | 8.00 |
| 160 | 0 | 0.00 | 82.00 |
| 200 | 0 | 0.00 | 87.00 |
| 240 | 0 | 0.00 | 88 |
| 280 | 0 | 0.00 | 99.7 |

TABLE 9

DMC Formation Using 5% MoO$_3$/SiO$_2$

| Temperature (° C.) | DMC Selectivity (%) | DMC Formation rate [nmol/gsec] | Methanol conversion (%) |
|---|---|---|---|
| 80 | 100 | 0.26 | 11.00 |
| 120 | 100 | 8.00 | 12.00 |
| 160 | 96 | 26.00 | 14.00 |
| 200 | 42 | 13.00 | 22.00 |
| 240 | 7.6 | 2.40 | 34 |
| 280 | 1 | 0.80 | 54 |

TABLE 10

DMC Formation Using 10% MoO$_3$/SiO$_2$

| Temperature (° C.) | DMC Selectivity (%) | DMC Formation rate [nmol/gsec] | Methanol conversion (%) |
|---|---|---|---|
| 80 | 100 | 0.36 | 12.00 |
| 120 | 100 | 10.00 | 13.00 |
| 160 | 92 | 30.00 | 22.00 |
| 200 | 30 | 9.00 | 28.00 |
| 240 | 3.3 | 1.60 | 40 |
| 280 | 0.45 | 0.35 | 61 |

TABLE 11

DMC Formation Using 50% MoO$_3$/SiO$_2$

| Temperature (° C.) | DMC Selectivity (%) | DMC Formation rate [nmol/gsec] | Methanol conversion (%) |
|---|---|---|---|
| 80 | 100 | 0.30 | 12.00 |
| 120 | 100 | 6.00 | 13.00 |
| 160 | 95 | 22.00 | 18.00 |
| 200 | 34 | 13.00 | 35.00 |
| 240 | 11 | 8.00 | 51 |
| 280 | 4 | 2.00 | 62 |

While DME and CO$_2$ were detected as the only DMC decomposition products, it may be concluded that the reaction on this catalyst takes place in a very similar way to the mechanism described for DMC synthesis over ZrO$_2$ (shown below in reaction XIV). The effectiveness of ZrO$_2$ was attributed to the presence of both acidic and basic sites. It was proposed that basic sites are required to activate methanol and CO$_2$, and that acidic sites are required to supply methyl groups from methanol in the last step of the reaction mechanism. The evidence from infrared spectroscopy, suggests that methoxy species are formed during adsorption of methanol on basic sites and rapidly converted to methyl carbonate species. Accordingly, CO$_2$ is activated and both oxygens of CO$_2$ take part in the formation of the DMC.

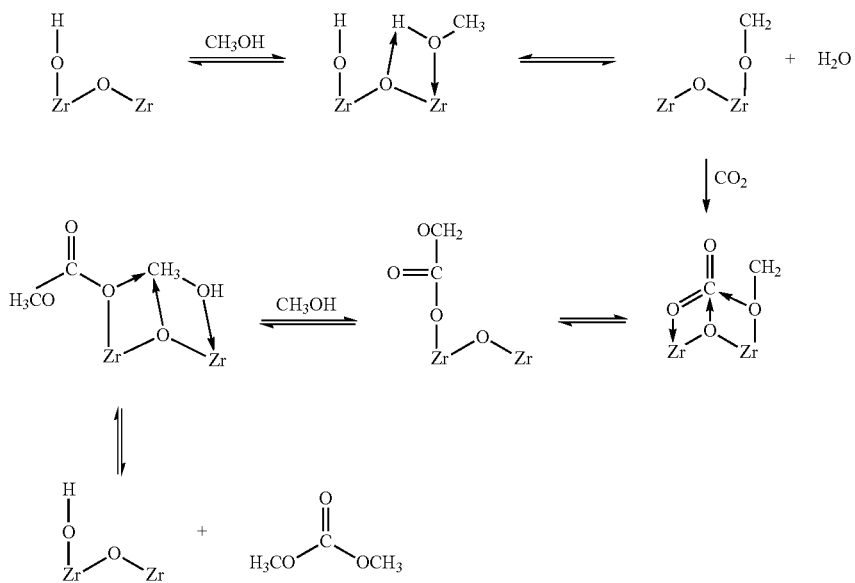

Reaction XIV: Proposed Mechanism for DMC Synthesis Over $ZrO_2$.

The results at different gas contents (FIG. 24B) demonstrate that DMC synthesis is affected by gas contents only to a small extent. The number of methoxy and activated $CO_2$ groups forming on the surface is the determining factor in the DMC formation.

Figure 26A:
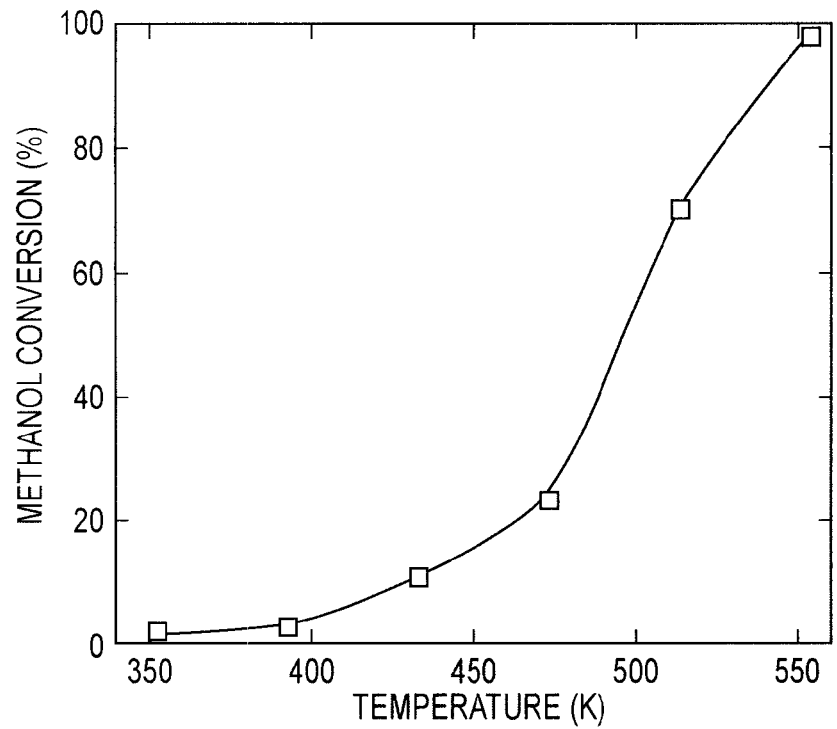
FIGS. 26A-26B are graphs illustrating methanol conversion and DMC/DME selectivity over pure $Mo_2C$.
Figure 26B:
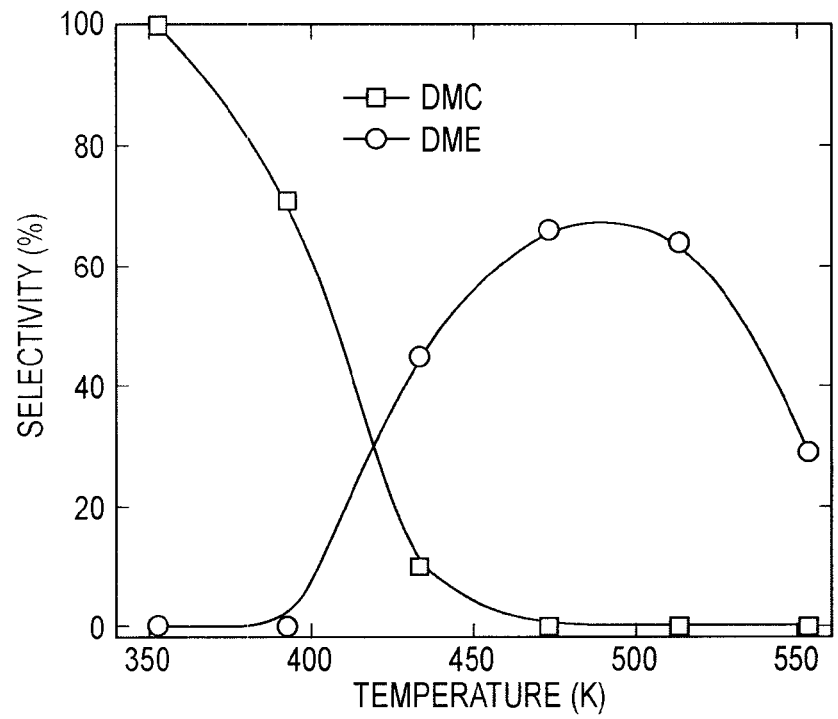
Figure 27A:
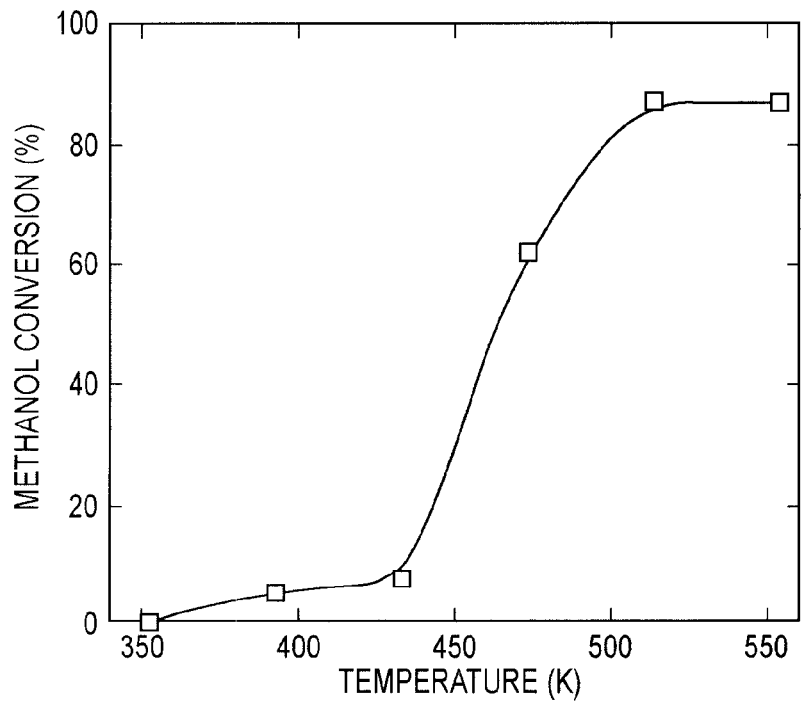
FIGS. 27A-27B are graphs illustrating methanol conversion and DME selectively over pure $Al_2O_3$.
Figure 27B:
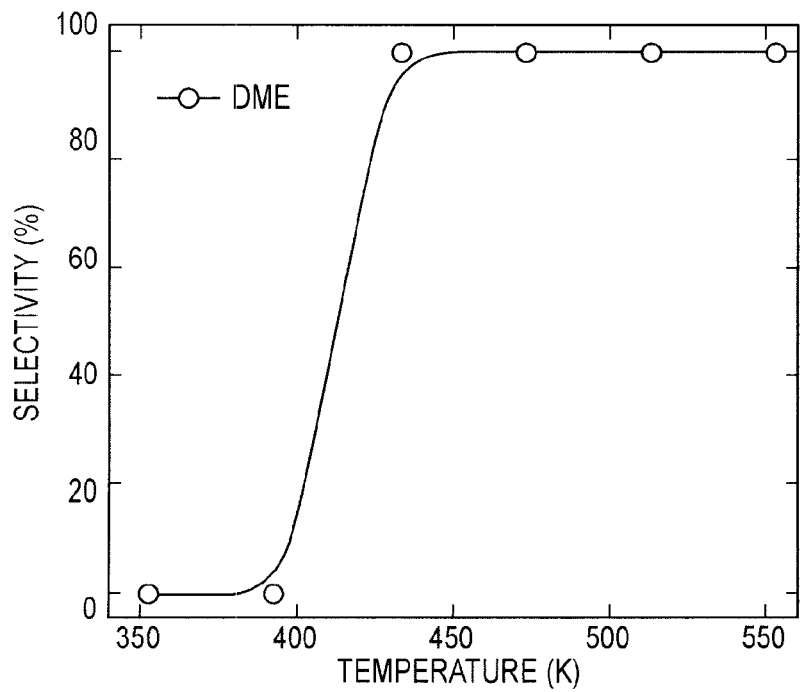

In the case of pure $Mo_2C$ (FIGS. 26A-26B), the results obtained were similar to those for 5% $Mo_2C/Al_2O_3$. The 100% DMC selectivity measured at the beginning of the reaction at 353 K (80° C.) (methanol conversion=2.7%) had decreased with temperature. Unlike the case of a supported catalyst, products from the decomposition of methanol (methane, formaldehyde) were detected at 393 K (120° C.). With a further increase of temperature, CO produced from the decomposition of $CO_2$ and methanol was also observed. From this it can be concluded that the support plays an important role in stabilizing and providing the surface with adsorbed methoxy group. This idea is also backed by the measurement taken on the $Al_2O_3$ support (FIGS. 27A-27B). At low temperatures (353-393 K) (80-120° C.), no product was detected on the support. With an increase in temperature (433-553 K) (160-280° C.), the decomposition products (hydrogen, CO, DME) appeared with DME as the favored product.

TPR of Methanol/$CO_2$

5% $Rh/Al_2O_3$

Figure 28:
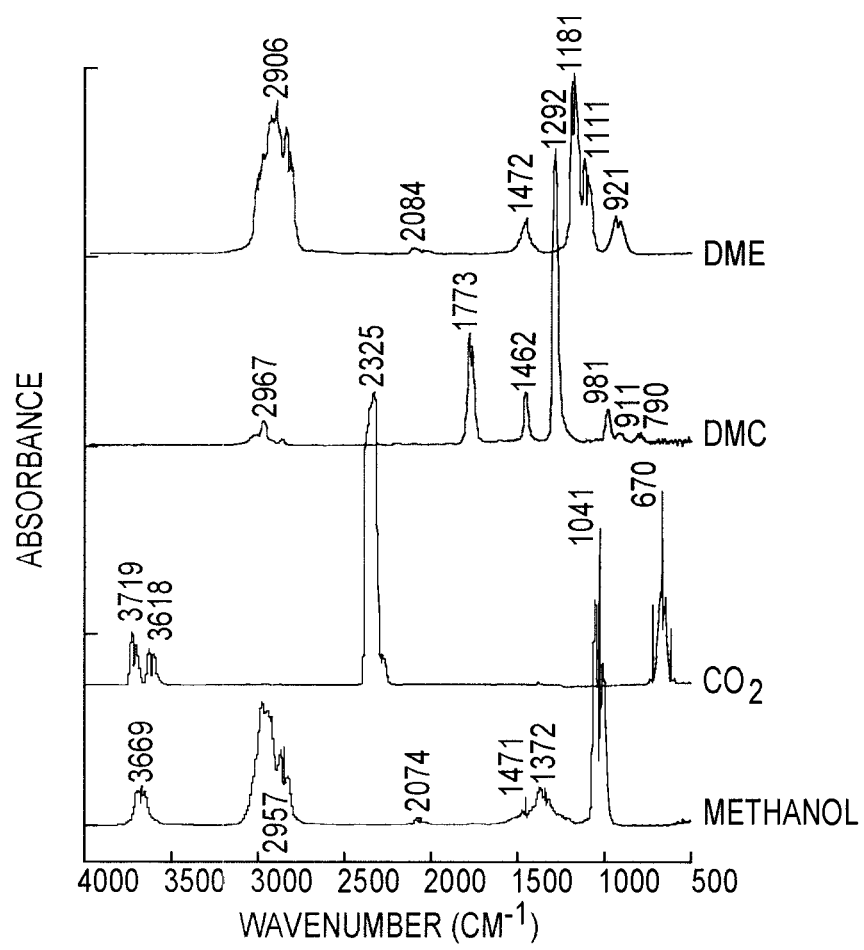
FIG. 28 is a graph of IR spectra of gaseous methanol, $CO_2$, DMC, and DME.

FIG. 28 shows the IR spectra of gaseous methanol, $CO_2$, DMC, and dimethyl ether (DME). The IR spectra show different IR features for each component, which were used to discern the overlapping of adsorbates with gaseous species during the DMC synthesis from methanol and $CO_2$.

Figure 29:
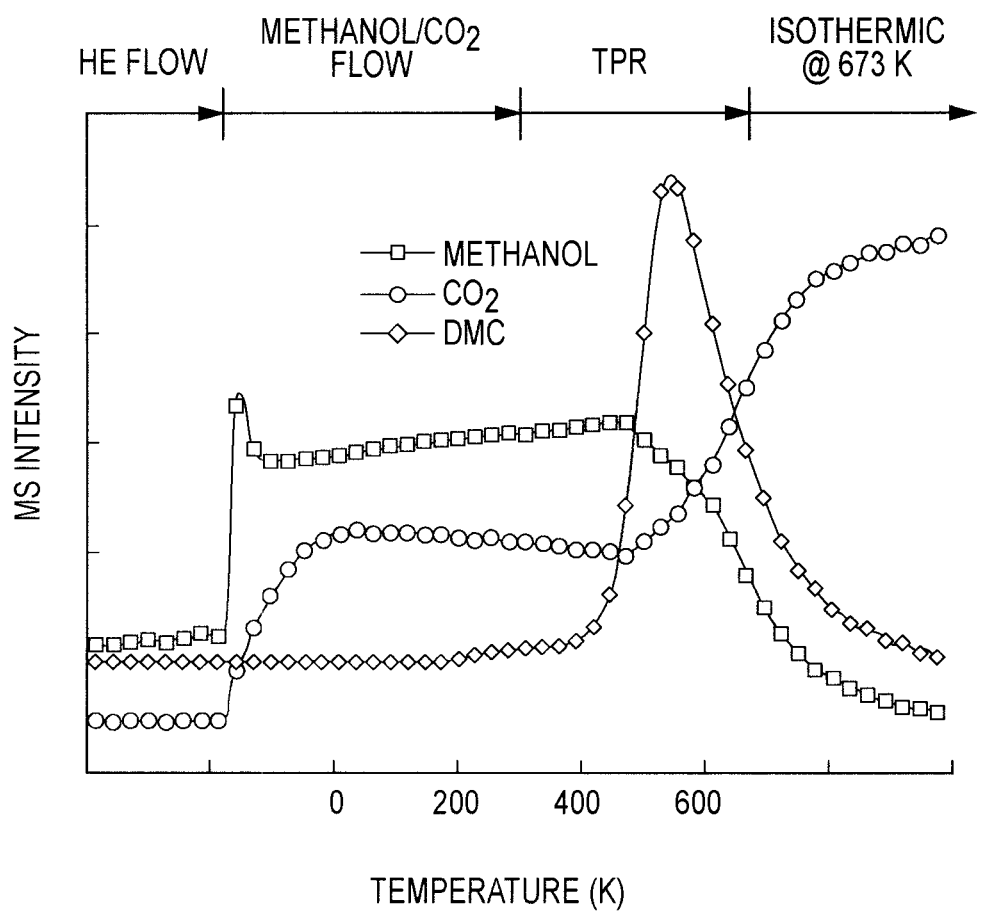
FIG. 29 is a graph of MS intensity during methanol-$CO_2$ TPR as a function of temperature.

FIG. 29 shows the MS intensity of the effluent from the IR reactor during the methanol-$CO_2$ TPR as a function of temperature. FIG. 29 shows that the decrease in methanol MS intensity was accompanied by an increase (formation) in that of DMC and $CO_2$. The formation of DMC reached a maximum at 541 K (268° C.). Above 541 K (268° C.), the $CO_2$ MS intensity continues to increase while those of methanol and DMC decreased. The decay in the MS intensity of DMC could be due to (i) thermodynamics or (ii) deactivation of the catalyst by water. Although both factors are important, the former is more notable. The dissociation and reaction of methanol caused a decrease in its MS intensity.

Figure 30:
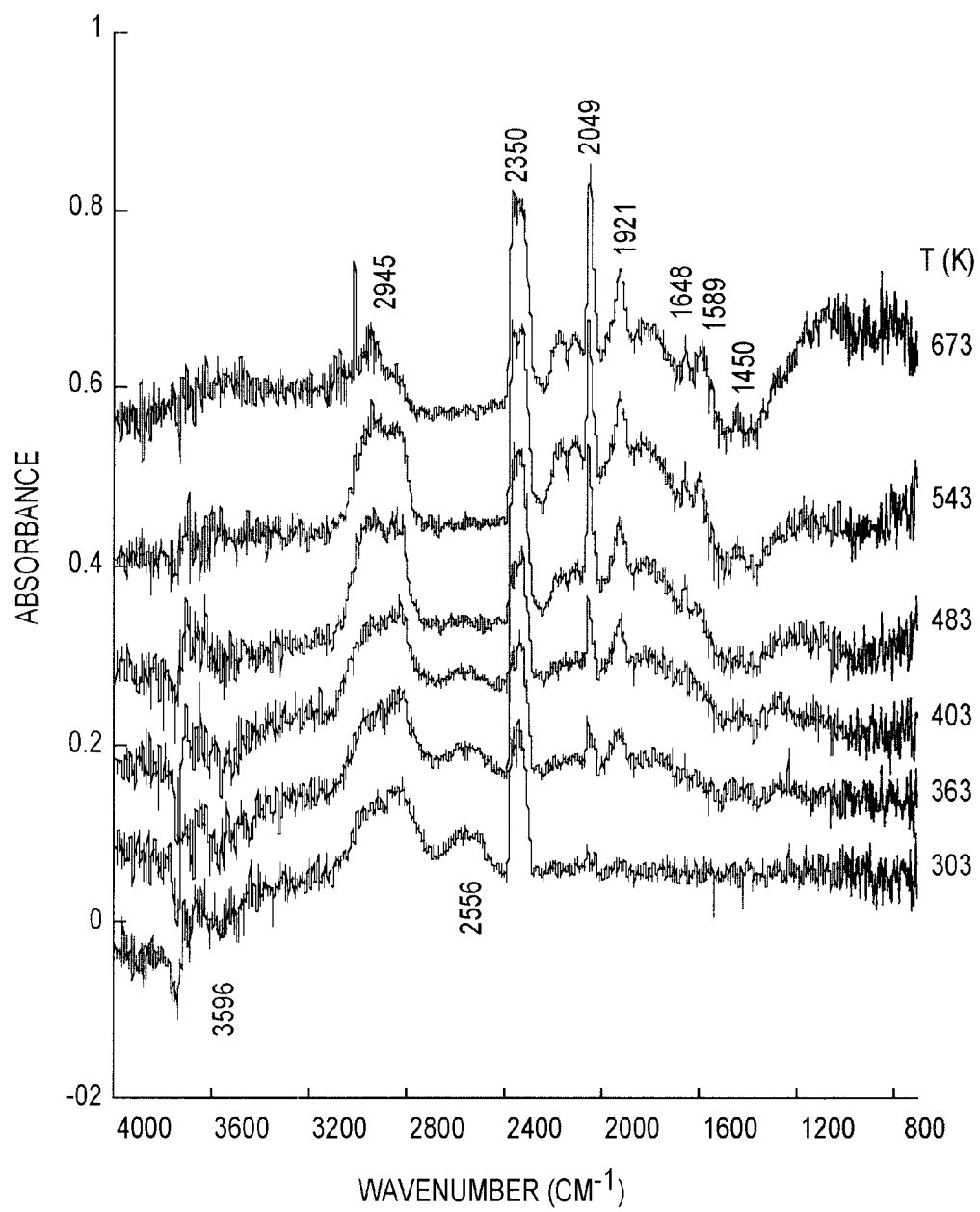
FIG. 30 is a graph of IR spectra during methanol-$CO_2$ TPR over $Rh/Al_2O_3$.

FIG. 30 shows the IR spectra of adsorbates during the methanol/$CO_2$ TPR as a function of temperature. The IR spectra of adsorbed methanol and $CO_2$ at 303 K (30° C.) show broad bands centered at 3596, 2945, and 2350 $cm^{-1}$ due to O—H, C—H in $CH_3O$ (methoxy species), and $CO_2$, respectively. Increasing the temperature to 363 K (90° C.) resulted in appearance of bands at 2049 and 1921 $cm^{-1}$. The bands centered at 2148, 1648, 1589, and 1450 $cm^{-1}$ appeared at 463 K (190° C.). The bands at 1450 and 1589 $cm^{-1}$ were assigned to C—H in $CH_3O$ (methoxy species) and OCO (formate), respectively. The appearance of bands at 2049 and 2148 $cm^{-1}$ was due to the formation of adsorbed CO on reduced Rh sites in a linear mod(Rh—C≡O) and gaseous CO, respectively. The band at 1648 $cm^{-1}$ can be assigned to the methoxy carbonate species ($CH_3OCOO$-M). The methoxy carbonate species on the surface of alumina was previously observed. It has been reported that the methoxy carbonate species was formed by the reaction between adsorbed methoxy species and $CO_2$ more easily than by the reaction between adsorbed $CO_2$ and methanol. This is probably because methanol can desorb $CO_2$ that adsorbed on the surface.

Formation of linear CO and gaseous CO indicates that methanol and/or $CO_2$ was dissociated over Rh surface. Spectroscopic studies on supported catalysts have shown that methanol dissociated to form linear CO, $CO_{(g)}$, and $CO_{2(g)}$, whereas $CO_2$ exhibited no evidence for its dissociation.

Figure 31:
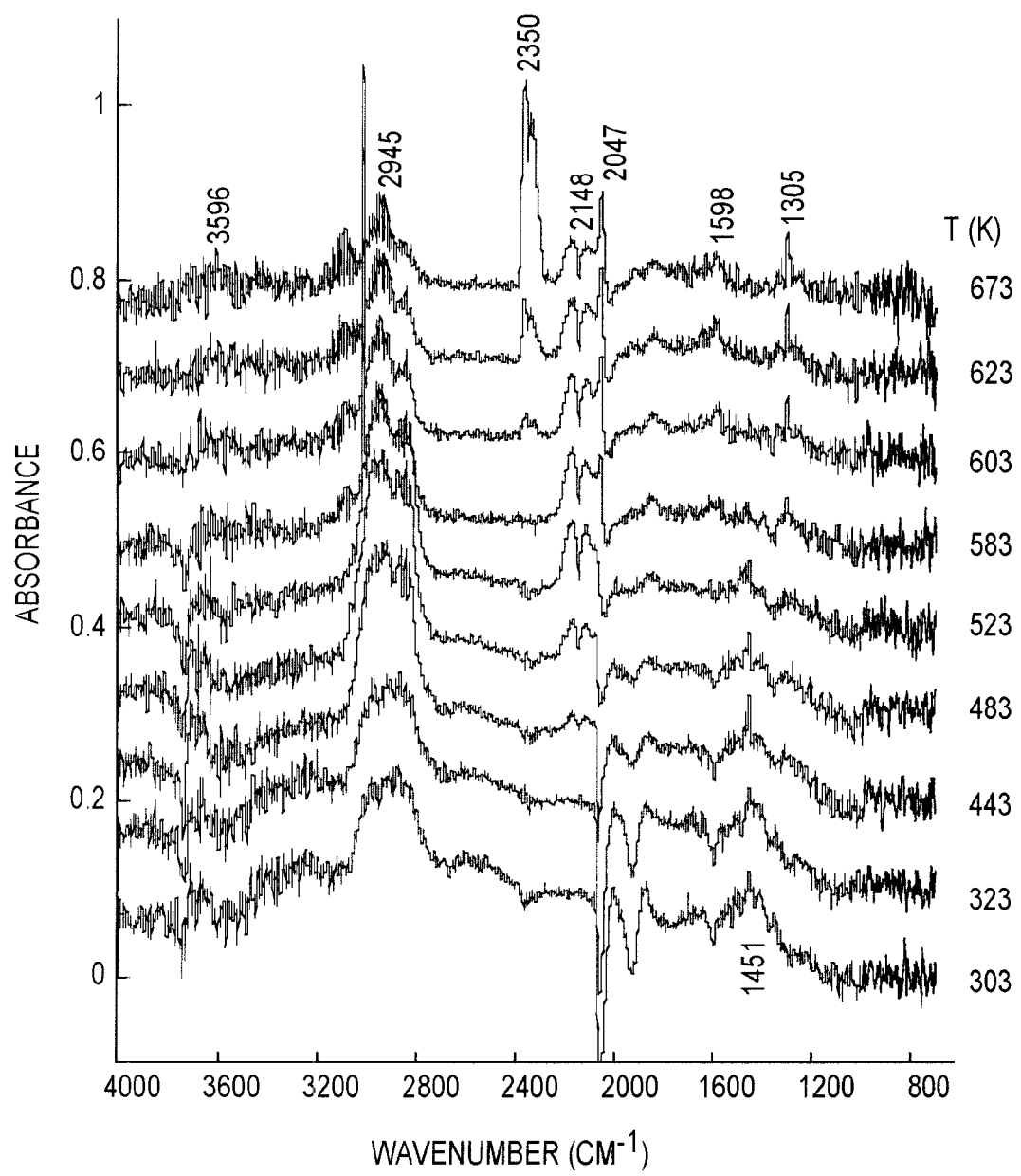
FIG. 31 is a graph of IR spectra during methanol TPR over $Rh/Al_2O_3$.
Figure 32:
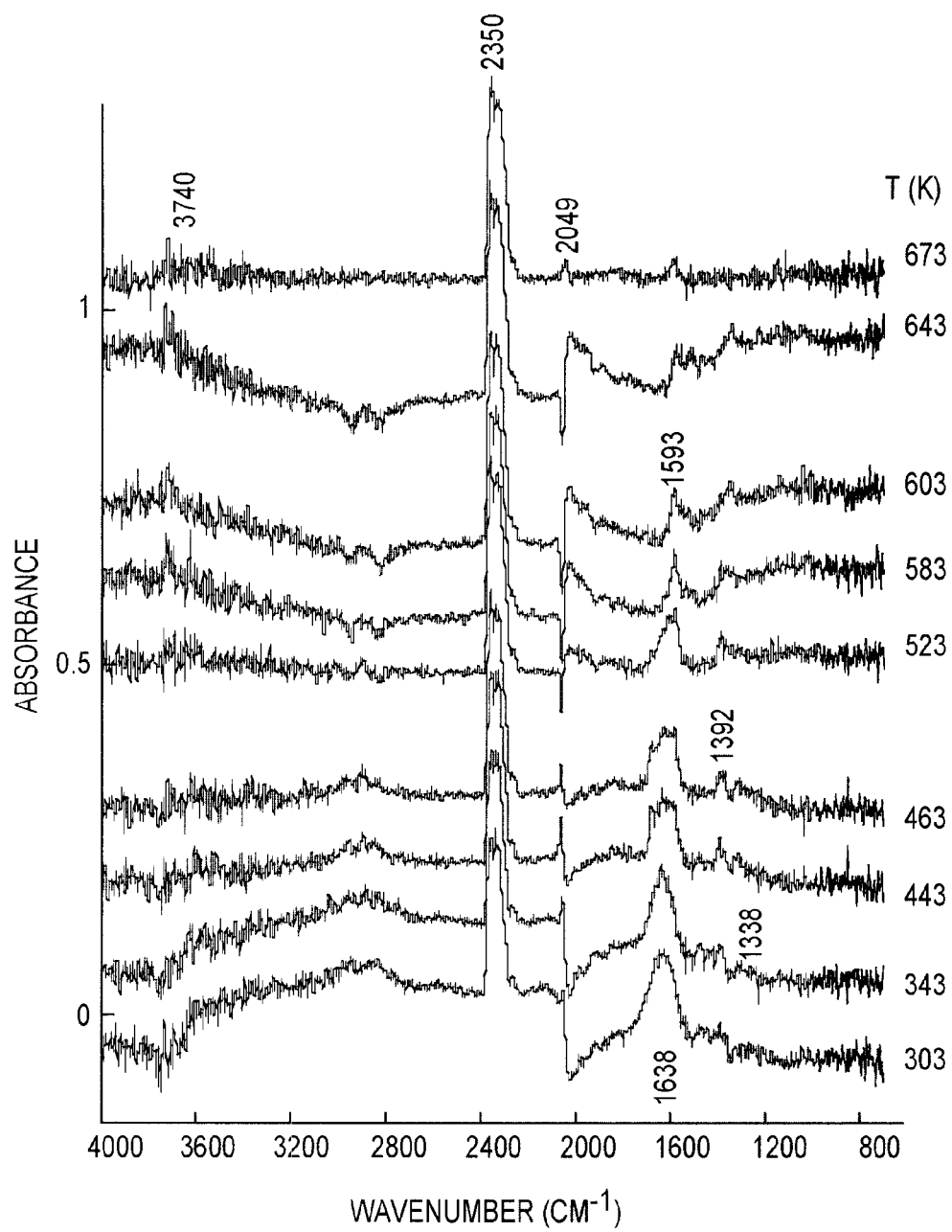
FIG. 32 is a graph of IR spectra during $CO_2$ TPR over $Rh/Al_2O_3$.
Figure 33:
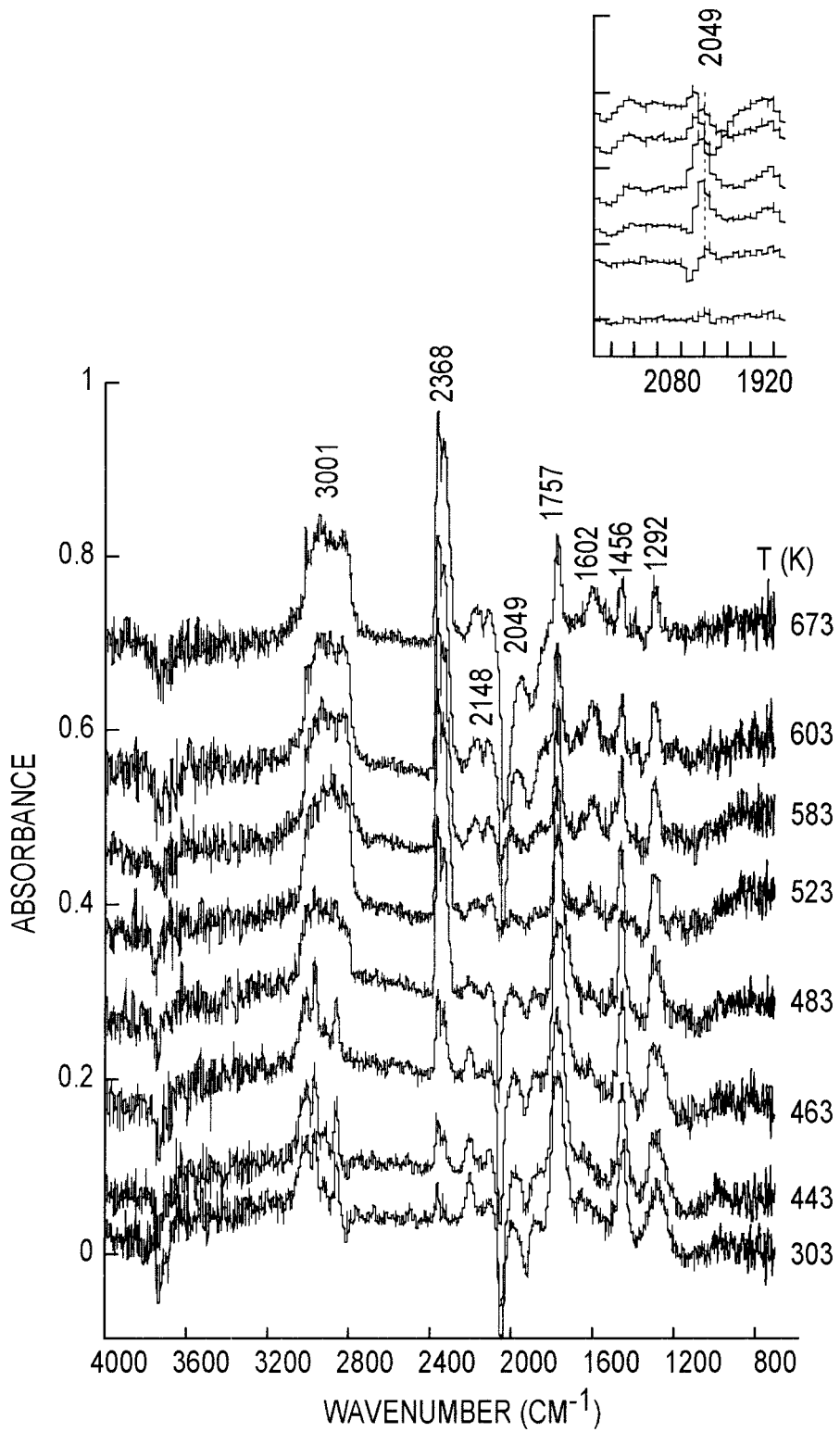
FIG. 33 is a graph of IR spectra during DMC TPR over $Rh/Al_2O_3$.

In order to elucidate the mechanism of the formation of linear CO, $CO_{(g)}$, and $CO_{2(g)}$, separate TPR experiments for methanol, $CO_2$, and DMC (FIGS. 31 to 33, respectively) were carried out. The IR spectra during the methanol TPR (FIG. 31) shows that linear CO and $CO_{(g)}$ appeared at 443 K (170° C.), and the appearance of $CO_{2(g)}$ started at 603 K (330° C.). Similarly, the TPR of DMC (FIG. 33) shows that linear CO (see the difference spectra presented in the inset in FIG. 32), $CO_{(g)}$, and $CO_{2(g)}$ were formed.

The $CO_2$ TPR (FIG. 32) shows no IR evidence of linear CO and $CO_{(g)}$. Absence of linear CO and $CO_{(g)}$ during the $CO_2$ TPR are in agreement with the results of $CO_2$ adsorption on various catalysts. It was reported that $CO_2$ dissociation enhanced only in the presence of adsorbed hydrogen. The following mechanism is valid for the formation of linear CO, $CO_{(g)}$, and $CO_2$ during the methanol dissociation in the present study:

$$CH_3OH_{(g)} \rightarrow CH_3OH_{ads} \quad\quad (XV)$$

$$CH_3OH_{ads} \rightarrow CH_3O_{ads}H_{ads} \quad\quad (XVI)$$

$$CH_3O_{ads} \rightarrow CO_{ads} + 3H_{ads} \quad\quad (XVII)$$

$$CO_{ads} \rightarrow CO_{(g)} \quad\quad (XVIII)$$

$$CO_{ads} + OH_{ads} \rightarrow CO_{2(ads)} + H_{ads} \quad\quad (XIX)$$

$$CO_{2(ads)} \rightarrow CO_{2(g)} \quad\quad (XX)$$

Reaction Mechanism

Figure 34:
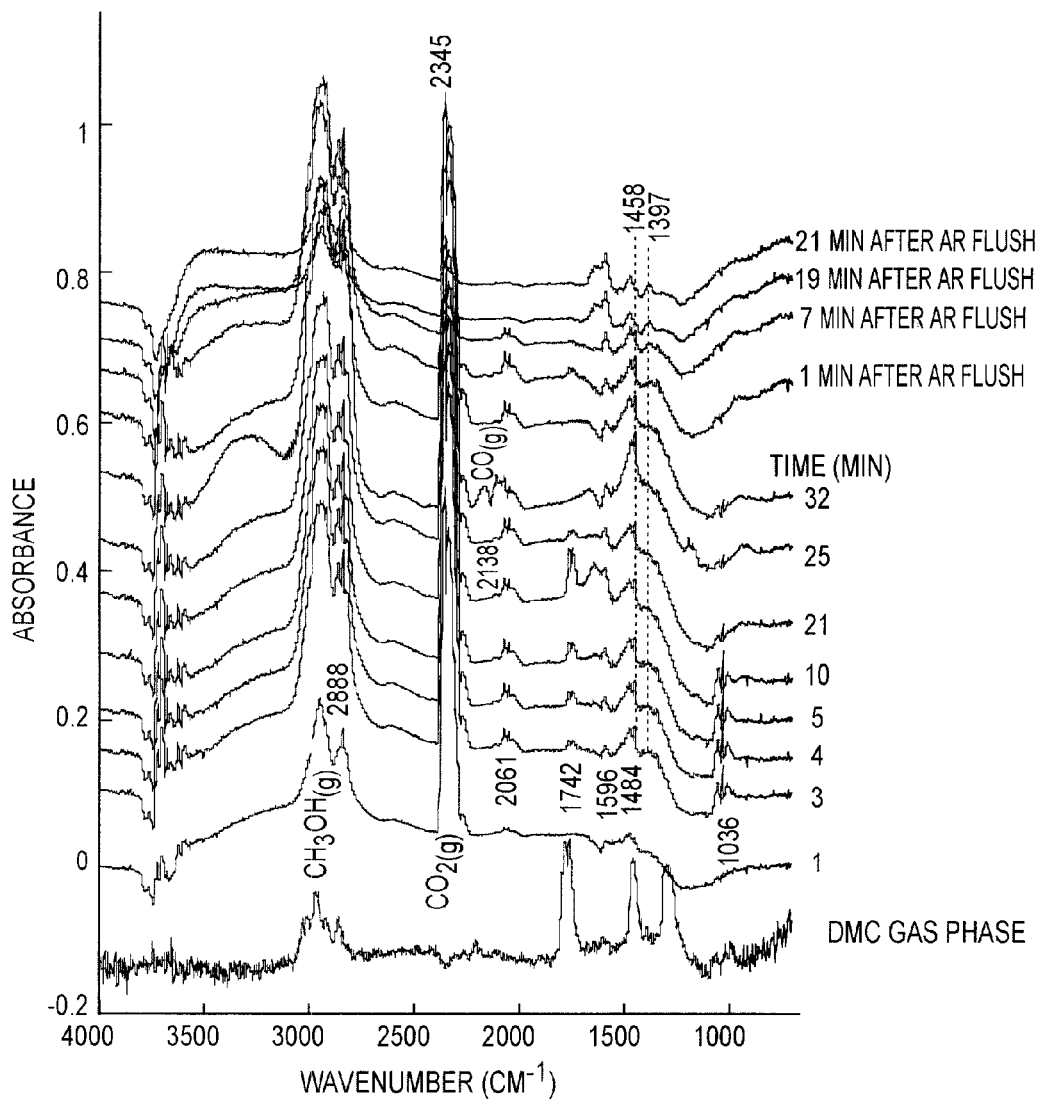
FIG. 34 is a graph of IR spectra during a methanol-$CO_2$ reaction over 5% $Mo_2C/Al_2O_3$.

FIG. 34 shows the IR spectra during methanol-$CO_2$ reaction over 5% $Mo_2C/Al_2O_3$ catalyst at 393 K (120° C.). The IR spectrum of gaseous DMC was included to elucidate the DMC formation. Introduction of methanol-$CO_2$ (2:1, 12 cm$^3$/min) resulted in appearance of gaseous methanol centered at 2888, 2061, 1036 cm$^{-1}$ and $CO_2$ centered at 2345 cm$^{-1}$. After 3 min, new bands at 1742 cm$^{-1}$ appeared due to gaseous DMC and 1596 and 1484, 1458 cm$^{-1}$ due to methoxy carbonate species. The intensity of the band 1742 cm$^{-1}$ increased with time and reached a maximum at 21 minutes. The decrease in the IR intensity of the 1742 cm$^{-1}$ band was accompanied by emergence of a gaseous CO band centered at 2138 cm$^{-1}$ and an increase the IR intensity of methoxy carbonate species at 1458 cm$^{-1}$.

In the direct synthesis of DMC from methanol and $CO_2$, it is important to activate methanol and $CO_2$ by basic sites and to supply the methyl species from methanol by acidic site as follows:

$$CH_3OH \rightarrow CH_3O^-_{(ads)} + H^+_{(ads)} \text{(Basic site)} \quad\quad (XXI)$$

$$CO_2 \rightarrow CO_{2(ads)} \text{(Basic site)} \quad\quad (XXII)$$

$$CH_3O^-_{(ads)} + CO_{2(ads)} \rightarrow CH_3OCO^-_{(ads)} \text{(Basic site)} \quad\quad (XXIII)$$

$$CH_3OH \rightarrow CH_3^+_{(abs)} + OH^-_{(abs)} \text{(Acidic site)} \quad\quad (XXIV)$$

$$CH_3OCO^-_{2(ads)} + CH_3^+_{(ads)} \rightarrow (CH_3O)_2CO \quad\quad (XXV)$$

$$H^+_{(ads)} + OH^-_{(ads)} \rightarrow H_2O \quad\quad (XXVI)$$

It is believed that the initial adsorption of $CH_3OH$ on catalyst surface occurs via the interaction of the O atom of $CH_3OH$ with a coordinately unsaturated Lewis acid center on the surface, which results in the formation of methoxy species. This process led to disappearance of surface OH groups and release of water.

Figure 35:
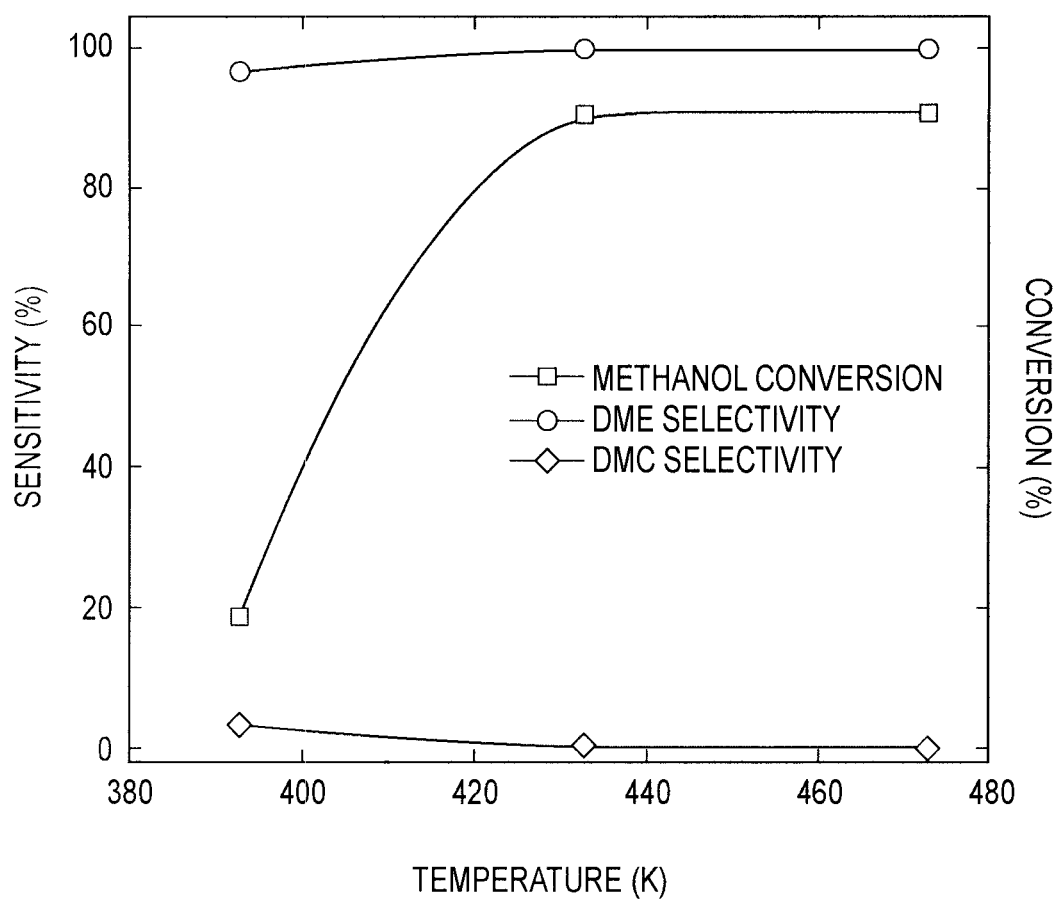
FIG. 35 is a graph of methanol conversion and DMC/DME selectivity during a methanol-CO reaction over 5% Rh/ZSM-5.
Figure 36:
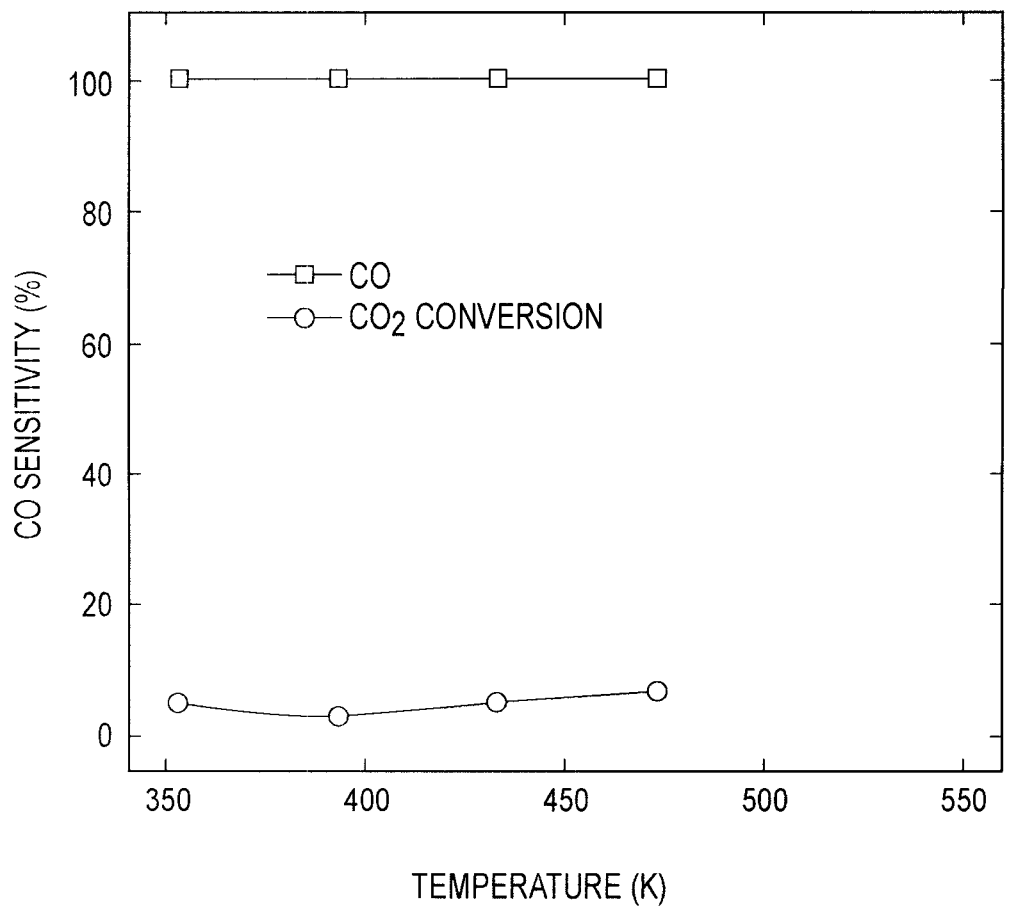
FIG. 36 is a graph of $CO_2$ conversion and CO selectivity during $CO_2$ decomposition over 5% Rh/ZSM-5.

DMC could be formed via: (i) insertion of adsorbed CO into two methoxy species or (ii) reaction of adsorbed $CO_2$ with methoxy species to form methoxy carbonate (reaction XXIII), which then reacts with methyl species (reaction XXV). It is believed that methoxy carbonate species are formed predominantly via $CO_2$ addition to methoxy species when $CH_3OH$ and $CO_2$ are passed concomitantly over the catalyst. To clarify this issue, the methanol-CO reaction was performed, during which DMC was not formed (FIG. 35). This suggests that insertion of adsorbed CO into two methoxy species to form DMC does not occur. The low conversion of $CO_2$ during its decomposition (FIG. 36) indicates that $CO_2$ participates in the reaction without dissociation into adsorbed CO and adsorbed O, which support the occurrence of reaction XXIII. The reaction of adsorbed $CO_2$ with methoxy species was supported by IR evidence and methanol-$CO_2$ reaction over different catalysts and support.

The $CO_2$ insertion into the $M-OCH_3$ bonds (reaction XXIII) has been reported for methoxy-containing complexes based on Mg or Ca. It has been proposed that the first step in the insertion of $CO_2$ into a $M-OCH_3$ bond involves an electron donor-acceptor interaction in which the alkoxy oxygen lone pairs act as the donor and the $CO_2$ carbon atom as the acceptor.

Conclusions

In this work, DMC synthesis was studied using a vapor phase flow reactor system in the presence of various catalysts. The effects of reaction conditions, promoters, and method of preparation on the catalyst performance were evaluated in terms of methanol conversion and DMC selectivity.

The following conclusions are apparent from the results of the present work.

Low temperatures, e.g. 353-433 K (80-160° C.), are favorable for DMC formation. However, DMC can generally be produced at a temperature within the range of from about 80° to about 280° C.

Among the various catalysts employed, Rh—, and $Mo_2C$— supported catalysts showed the best catalytic performance in the DMC synthesis.

The Temperature-Programmed Reaction (TPR) showed that methanol was dissociated into methoxy species and linear CO.

Adsorbed methoxy species and the activated $CO_2$ play an important role in the DMC synthesis and their population is the determining factor in DMC formation.

The effectiveness of any catalyst for DMC synthesis is attributed to the presence of both acidic and basic sites. Basic sites are required to activate methanol and $CO_2$, and acidic sites are required to supply methyl groups from methanol in the last step of the reaction mechanism.

DMC forms via reaction of adsorbed $CO_2$ with methoxy species to form methoxy carbonate (($CH_3O)CO_2$ (active adsorbate), which then reacts with methyl species to form DMC.

DMC formation is a reversible process, which became less pronounced with the increase of temperature.

As far as DMC yield is concerned, the $Al_2O_3$ support was the most effective in the case of $Mo_2C$ catalyst.

The reason for inferiority of certain catalysts prepared by a sol-gel method could be due to the presence of water in the reaction system and not to the absence of well controlled acidic and basic sites.

Loss of surface chloride was the reason of the catalyst system deactivation in the DMC synthesis.

Removal of water is necessary to shift the reaction toward the DMC formation.

The preferred methods for producing DMC can be carried out in a flow system, i.e. a continuous or semi-continuous system. Preferably, the methods are performed at pressures of from about 0.9 atmospheres to about 1.5 atmospheres. In certain embodiments, the methods are performed at about 1 atmosphere pressure.

EXAMPLES

Catalyst Preparation

Two methods of catalyst preparation were used in the present work:

Impregnation Method

Impregnation is an important and widely used method in preparing catalysts. It is the simplest method of producing catalyst. It allows an accurate adjustment of salt, and the active components/support ratio.

Impregnation is achieved by filling the pores of a support with a solution of a metal salt from which the solvent is subsequently evaporated. The technique can be classified as dry or wet impregnation based on the initial state of the support.

Sol-Gel Method

The sol-gel process is a technique for the preparation and fabrication of inorganic oxides of extremely high purity and homogeneity. The word sol implies a dispersion of colloidal in a liquid. Colloids are in turn described as solid particles with dimensions in the range of 10 to 1000 Å, each with from about $10^3$ to about $10^9$ atoms. When the viscosity of a sol increases sufficiently, usually by the loss of its liquid phase and or polymerization of the solid particles, it becomes a porous solid body, which is termed a gel.

Rh-, Pd-, Pt-Supported Catalysts

The Rh-, Pd-, Pt-containing catalysts with different promoters, e.g., Ce, K, Ni, were prepared by incipient wetness impregnation onto $Al_2O_3$, $SiO_2$, $ZrO_2$, $V_2O_5$, $TiO_2$, ZSM-5 or carbon. The catalyst was dried overnight in air at room temperature and calcined by flowing air at 673 K (400° C.) for 3 hours and then reduced by flowing $H_2$ at 673 K (400° C.) for 3 hours.

$MoO_3$ and $Mo_2C$-Supported Catalysts $MoO_3$-containing catalysts were prepared by impregnating $Al_2O_3$, $SiO_2$, $ZrO_2$, $V_2O_5$, $TiO_2$, or ZSM-5 (Sigma-Aldrich Chemicals) with a basic solution of ammonium heptamolybdate to yield different weight percentage of $MoO_3$ (Sigma-Aldrich Chemicals). The suspension was dried at 373 K (100° C.) and calcined at 863 K (590° C.) for 5 hours.

Supported $Mo_2C$ catalysts were prepared by the carburization of calcined the supported $MoO_3$ catalysts by ethane. $MoO_3$-containing samples were heated under 10% (v/v) $C_2H_6/H_2$, from room temperature to 900 K (627° C.) at a heating rate of 0.8 K $min^{-1}$. After preparation, the catalysts were cooled down to room temperature under argon. The carbides were passivated in flowing 1% $O_2$/Ar at 300 K (27° C.). Before the catalytic experiments, the samples were treated with $H_2$ at 873 K (600° C.) for 1 hour to remove any excess carbon.

Catalysts Prepared by Sol-Gel Method

Alumina is formed through preparing hydrolyzed aluminum precursors, where stirring and pH control affect the properties. The synthesis step is followed by aging, solvent washing, drying and dehydration. The $Rh/Al_2O_3$, $Pt/Al_2O_3$, $Pd/Al_2O_3$, and $Ni/Al_2O_3$ samples were prepared and denoted as Rh/, Pd/, Pt/, $Ni/Al_2O_3$ (sol-gel). 13.5 g from aluminum tri-sec-butoxde (ASB) (from Sigma-Aldrich Chemicals) was dissolved in 73.3 g of 2-butanol (from Scharlau Chemicals). The mixture was continuously stirred till the ASB dissolved completely (designated as solution 1). The chloride form of Rh, Pd, Pt, or Ni (Sigma-Aldrich Chemicals of Barcelona, Spain) was dissolved in water and mixed with solution 1 for 1 hour. The sample was covered and allowed to be in open air for 24 h at room temperature before it was dried at 353 K (80° C.) for 24 hours. Before any experiment, the catalyst sample was calcined at 823 K (550° C.) and reduced at 673 K (400° C.)

Catalyst Characterization

Scanning Electron Microscopy (SEM)

SEM provides direct topographical images of the solid structure, which are formed by back-scattered primary electrons. In this method, the overall contrast is due to differential absorption of photons or particle (amplitude contrast) and more importantly diffraction phenomena (phase contrast). SEM can provide magnification powers of greater than three hundred thousand. Powdered samples were attached to 12.5 mm diameter aluminum stubs via double sticking 12 mm diameter carbon tabs. The particles were viewed by SEM (Cambridge S360 from Cambridge Scientific Instruments Co. of the UK) operated at the following settings: Accelerating Voltage=20 kV, Working Distance=15 mm, and Image Resolution: Ultrafine. The images were recorded in secondary electron imaging mode (SE) at different magnifications.

Energy Dispersive X-ray Spectroscopy (EDX)

SEM-EDX was used for elemental analysis of the catalyst to investigate the presence of any impurities or contaminants that might adversely affect the catalyst. Multiple particles were analyzed for elemental composition by EDX (Oxford ISIS300, Instrument ID: EDX-1) attached to SEM. EDX analysis was performed on flat regions (where possible) in area mode at settings: Accelerating Voltage=20 kV and Working Distance=25 mm. The elemental composition of metals was estimated by EDX system software and pure metal standard spectra.

Surface Area, Pore Volume, and Pore Size

The physical properties of the catalysts (i.e., surface area, pore volume, and pore size) were determined by Quantachrome Autosorb automated gas adsorption system using nitrogen gas.

Experimental System

Figure 37A:
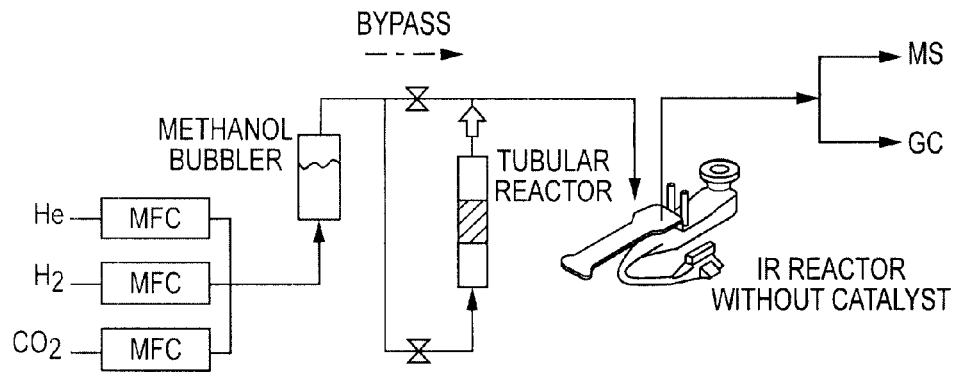
FIGS. 37A-37B are schematic illustrations of two schemes for catalyst screening and activity studies, and TPR studies.
Figure 37B:
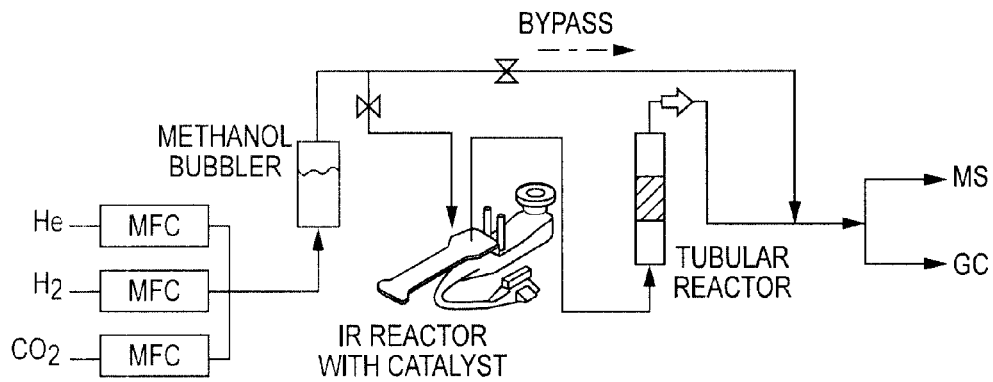

The experimental system shown in FIGS. 37A-37B included (i) a gas flow section with a 4-port switching valve and 6-port pulsing valve, (ii) an in situ IR reactor with/without catalyst, and (iii) an analysis section.

Analysis Section

The analysis section included an IR spectrometer to measure the adsorption intensity and vibrational frequency (wavenumber, $cm^{-1}$) of adsorbed and gaseous species on the catalyst surface, a gas chromatograph to measure the steady-state gas phase concentrations of the effluent, and a mass spectrometer to measure the transient effluent concentrations of gaseous products. The flow rates of the gasses were controlled by mass flow controllers (Omega 750 from Omega of Stamford, Conn.).

Infrared Spectrometer

The effluent gases from the reactor were sent to an environmental chamber (IR reactor cell) placed in the FTIR compartment. The steady-state and transient IR spectra were collected by a Thermo Nicolet Nexus 670 FTIR spectrometer equipped with a MCT detector that was cooled with liquid nitrogen. A high pressure/high temperature chamber (see FIGS. 37A-37B) fitted with ZnSe windows, was utilized as an IR reactor cell for in situ reaction studies. The IR reactor cell was heated by a temperature controller. The lines from the bubbler to the IR reactor were wrapped with heating tape and insulated with general purpose insulating wrap. For steady-state spectra, 64 scans were co-added at a resolution of 4 $cm^{-1}$. Co-adding a large number of scans increased the signal to noise ratio (S/N), but required longer sampling time, resulting in the loss of the transient information.

Gas Chromatograph

The effluent gases of the IR reactor cell were sent to a Varian CP-3800 gas chromatograph (GC) for determination of the steady-state effluent concentrations of methanol, $CO_2$, and DMC. The gas chromatograph contained a thermal conductivity detector (TCD) and flame ionization detector (FID).

Mass Spectrometer

The effluent gases of the IR reactor cell were also sent to the mass spectrometer PRISMA QMS-200 M quadruple with a continuous secondary electron multiplier (SEM). Careful selection of the mass/charge (m/e) signals for the gaseous products is required to prevent overlapping of the responses. Prior to the investigation, Helium was used to purge the sampling line. A four-port valve allowed for an efficient switch from Helium to the reactor effluent. Helium was fed to the ⅛ inch sampling line to prevent air from entering the mass spectrometer and oxidizing the filament when the mass spectrometer sampling valve is open for uptaking the sample gases. The gaseous stream from the ⅛ inch line entered a capillary line that is 2 mm OD and 0.15 mm ID, and then a two-stage differentially pumped gas inlet system (Balzers GES-010) for continuously drawing the gas sample into a medium vacuum of approximately 0.7 mbar by a rotary vane pump. The valve to the mass spectrometer vacuum chamber had an aperture that allowed about 2% of the gas in the medium vacuum to enter. After entering through the sampling valve, the sample gas was transported to the quadruple analyzer. Data acquisition was conducted by the QUADSTAR-522 software package for collection of mass spectrometric data. This program allows for the measurement of up to 200 m/e ratios as a function of time. The gaseous MS responses for m/e ratios corresponding to methanol (m/e=29, 31, 32), $CO_2$ (m/e=44, 22, 28), and DMC (m/e=45, 59, 90) were monitored.

Catalysts Screening and Testing

FIG. 37A shows the schematic used in the catalyst screening and testing. A 500 mg of catalyst was loaded into a tubular reactor (I.D. of 8 mm) inside a GC furnace, and reduced with $H_2$ or calcined with air depending on the nature of catalyst. A total of 12 cm³/min of $CO_2$/He (1:9 cm³/min) was passed through a bubbler containing methanol and sent to the reactor. The reaction was carried out at 363 K (90° C.), 383 K (110° C.), 403 K (130° C.), to 573 K (300° C.) for 40 minutes at each temperature level. The effluent of reactor was sent to the empty IR reactor cell and the GC to determine the amount of DMC. The selectivity for reaction products, Si and Formation molar flow rate of DMC were defined as:

$$\text{Selectivity (\%)} = \frac{\text{No. of carbon in } i * (\text{Formation rate of } i \text{ mol/g. sec}) * 100}{\Sigma \text{ Carbon in product}}$$

and $$\text{Formation molar flow rate of } DMC = \frac{(\text{mol of } DMC \text{ from } GC) * (\text{Total flow rate ml/min})}{(\text{Volume of } GC \text{ sampling loop ml}) * (60 \text{ min/sec}) * g. \text{ cat}}$$

The Temperature-Programmed Reaction (TPR) Studies

The TPR is a useful technique to scan a wide range of temperatures under which a reaction may take place. It may also provide information about active adsorbate(s) that participate in the reaction and spectator adsorbate.

FIG. 37B shows the schematic used in the TPR studies. The catalyst powder (40 mg) was placed into the IR reactor cell, and an additional catalyst (160 mg) was placed into a tubular reactor to increase the reactant conversion and product formation for GC and MS measurements. A total of 12 cm³/min of $CO_2$/He (1:9 cm³/min) was passed through a bubbler containing methanol and sent to the IR reactor with catalyst.

Prior to TPR, the catalyst was reduced by $H_2$ at 673 K (400° C.) for 2 hours and IR background spectra were collected while the catalyst was cooled in He flow from 673 K (400° C.) to 303 K (30° C.). $CO_2$ and He were flowed into a methanol bubbler then to the reactor. The effluent of reactor was sent to the GC and the MS. Upon the MS intensities of gaseous species becoming constant, the temperature was increased from 303 K (30° C.) to 673 K (400° C.) at 8 K/minute. The background spectra were subtracted from IR spectra collected during the TPR.

Many other benefits will no doubt become apparent from future application and development of this technology.

All patents, published applications, and articles noted herein are hereby incorporated by reference in their entirety.

It will be understood that any one or more feature or component of one embodiment described herein can be combined with one or more other features or components of another embodiment. Thus, the present invention includes any and all combinations of components or features of the embodiments described herein.

As described hereinabove, the present invention solves many problems associated with previously known catalysts and methodologies. However, it will be appreciated that various changes in the details, materials and arrangements of parts, which have been herein described and illustrated in order to explain the nature of the invention, may be made by those skilled in the art without departing from the principle and scope of the invention, as expressed in the appended claims.

What is claimed is:

1. A method for producing dimethyl carbonate, the method comprising:
   providing effective amounts of methanol and carbon dioxide to a reaction vessel;
   reacting methanol and carbon dioxide at atmospheric pressure in the presence of a heterogeneous catalyst in the reaction vessel to produce dimethyl carbonate;
   wherein the heterogeneous catalyst is selected from the group consisting of $Pd/Al_2O_3$, $Pt/Al_2O_3$, $Ni/Al_2O_3$, $Ni/SiO_2$—$Al_2O_3$, $Mo_2C/Al_2O_3$, $Pd/V_2O_5$, $Pd/TiO_2$, $Pd/TiO_2$—$V_2O_5$, $Pd/TiO_2$—$ZrO_2$, $Pt/Al_2O_3$, $Re/Al_2O_3$, $MoO_3/Al_2O_3$, $MoO_3/ZSM$-5, and $MoO_3/SiO_2$.

2. The method of claim 1, wherein the support of the catalyst is formed by a sol-gel method.

3. The method of claim 1 wherein the reaction is performed at a temperature of from about 80° to about 280° C.

4. The method of claim 1 wherein water is produced as a by-product in the production of dimethyl carbonate, the method further comprising:
   removing at least a portion of the water to thereby increase production of dimethyl carbonate.

5. The method of claim 4 wherein the removing at least a portion of the water is performed by circulating a reaction mixture through a dehydrating tube.

6. A method for producing dimethyl carbonate using a heterogeneous catalyst, the method comprising:
   providing an effective amount of methanol to a reaction vessel;
   providing an effective amount of carbon dioxide to the reaction vessel;
   reacting the methanol and the carbon dioxide at atmospheric pressure in the presence of a heterogeneous catalyst to thereby produce dimethyl carbonate;
   wherein the heterogeneous catalyst provides acidic reaction sites and basic reaction sites; and
   wherein the heterogeneous catalyst is selected from the group consisting of $Pd/Al_2O_3$, $Pt/Al_2O_3$, $Ni/Al_2O_3$, $Ni/SiO_2$—$Al_2O_3$, $Mo_2C/Al_2O_3$, $Pd/V_2O_5$, $Pd/TiO_2$, $Pd/TiO_2$—$V_2O_5$, $Pd/TiO_2$—$ZrO_2$, $Pt/Al_2O_3$, $Re/Al_2O_3$, $MoO_3/Al_2O_3$, $MoO_3/ZSM$-5, and $MoO_3/SiO_2$.

7. The method of claim 6 wherein the support of the catalyst is formed by a sol-gel method.

8. The method of claim 6 wherein the reaction is performed at a temperature of from about 80° to about 280° C.

9. The method of claim 6 wherein water is produced as a by-product in the production of dimethyl carbonate, the method further comprising:
   removing at least a portion of the water to thereby increase production of dimethyl carbonate.

10. The method of claim 9 wherein the removing at least a portion of the water is performed by circulating a reaction mixture through a dehydrating tube.

11. A method for producing dimethyl carbonate, the method comprising:
   providing effective amounts of methanol and carbon dioxide to a reaction vessel;
   reacting methanol and carbon dioxide at atmospheric pressure in the presence of a heterogeneous catalyst in the reaction vessel to produce dimethyl carbonate, wherein the heterogeneous catalyst includes a catalyst and a support, and the heterogeneous catalyst is selected from the group consisting of $Pd/Al_2O_3$, $Pt/Al_2O_3$, $Ni/Al_2O_3$, $Ni/SiO_2$—$Al_2O_3$, $Mo_2C/Al_2O_3$, $Pd/V_2O_5$, $Pd/TiO_2$, $Pd/TiO_2$—$V_2O_5$, $Pd/TiO_2$—$ZrO_2$, $Pt/Al_2O_3$, $Re/Al_2O_3$, $MoO_3/Al_2O_3$, $MoO_3/ZSM$-5, and $MoO_3/SiO_2$.

* * * * *